(12) United States Patent
Bae et al.

(10) Patent No.: US 11,484,601 B2
(45) Date of Patent: Nov. 1, 2022

(54) TARGETING M2-LIKE TUMOR-ASSOCIATED MACROPHAGES BY USING MELITTIN-BASED PROAPOPTOTIC PEPTIDE

(71) Applicant: TWINPIGBIOLAB INC., Hanam-si (KR)

(72) Inventors: Hyun-Su Bae, Seoul (KR); Chan-Ju Lee, Goyang-si (KR); Jin-Hyun Jeong, Goyang-si (KR); Do-Ha Lee, Changwon-si (KR); Jeong-Dong Kim, Incheon (KR)

(73) Assignee: TWINPIGBIOLAB INC., Hanam-si (KR)

( * ) Notice: Subject to any disclaimer, the term of this patent is extended or adjusted under 35 U.S.C. 154(b) by 57 days.

(21) Appl. No.: 17/052,943

(22) PCT Filed: May 7, 2019

(86) PCT No.: PCT/KR2019/005438
§ 371 (c)(1),
(2) Date: Nov. 4, 2020

(87) PCT Pub. No.: WO2019/212324
PCT Pub. Date: Nov. 7, 2019

(65) Prior Publication Data
US 2021/0244823 A1    Aug. 12, 2021

(30) Foreign Application Priority Data
May 4, 2018    (KR) ........................ 10-2018-0051800

(51) Int. Cl.
*A61K 38/00*    (2006.01)
*A61K 47/64*    (2017.01)
*A61P 35/00*    (2006.01)
*A61K 38/17*    (2006.01)
*A61K 38/10*    (2006.01)

(52) U.S. Cl.
CPC .............. *A61K 47/64* (2017.08); *A61K 38/10* (2013.01); *A61K 38/1767* (2013.01); *A61K 47/6415* (2017.08); *A61P 35/00* (2018.01)

(58) Field of Classification Search
CPC ..... A61K 47/64; A61K 47/6415; A61K 38/10
See application file for complete search history.

(56) References Cited

U.S. PATENT DOCUMENTS

2016/0263235 A1    9/2016    Castaigne et al.

FOREIGN PATENT DOCUMENTS

EP    0 359 347 B1    12/1992
JP    2002-543111 A    12/2002

OTHER PUBLICATIONS

Shin et al. Pharm Res (2016) 33:2218-2228.*
Huang et al. (2017). Tumor-penetrating peptide fused to a pro-apoptotic peptide facilitates effective gastric cancer therapy. Oncology Reports, 37, 2063-2070. https://doi.org/10.3892/or.2017.5440.*
Chanju Lee et al., "Development of melittin-based anti-cancer drug for targeting tumor-associated macrophages", The Journal of Immunology, 2018, vol. 200 (1 Supplement), No. 56.22, 2 pages total.
Islam Rady et al., "Melittin, a major peptide component of bee venom, and its conjugates in cancer therapy", Cancer Letters, 2017, vol. 402, pp. 16-31, 17 pages total.
Walter J. Gensler et al., "Preparation of Testosteronephosporhic Acid", Journal of the American Chemical Societ, 1954, vol. 76, No. 23. pp. 6192-6193, 3 pages total.
"Melatin", Nikkei Dictionary, 1961, No. J11.783H, 2 pages total.
Communication dated Nov. 16, 2021 from the Japanese Patent Office in Application No. 2021-512351.
Chanju Lee et al., "Development of melittin-based anti-cancer drug for targeting tumor-associated macrophages", The Journal of Immunology, May 1, 2018, vol. 200 (1 Supplement), 56.22, abstract.
Islam Rady et al., "Melittin, a major peptide component of bee venom, and its conjugates in cancer therapy", Cancer Letters, 2017, pp. 16-31, vol. 402.
Chanju Lee et al., "Melittin suppresses tumor progression by regulating tumor-associated macrophages in a Lewis lung carcinoma mouse model", Oncotarget, 2017, pp. 54951-54965, vol. 8, No. 33.
International Search Report of PCT/KR2019/005438 dated Aug. 26, 2019 [PCT/ISA/210].

* cited by examiner

*Primary Examiner* — Jeanette M Lieb
(74) *Attorney, Agent, or Firm* — Sughrue Mion, PLLC

(57)    ABSTRACT

The present invention relates to a melittin-anticancer drug conjugate in which melittin and an anticancer drug are conjugated, and to a method of preparing a melittin-anticancer drug conjugate by connecting melittin and an anticancer drug. A conjugate of the present invention is an anticancer material for targeting M2-type tumor-associated macrophages (TAM) and exhibits an excellent effect of selectively selecting M2-type tumor-associated macrophages (TAM), and thus may be used for a use of drug delivery for targeting M2-type tumor-associated macrophages.

17 Claims, 15 Drawing Sheets
Specification includes a Sequence Listing.

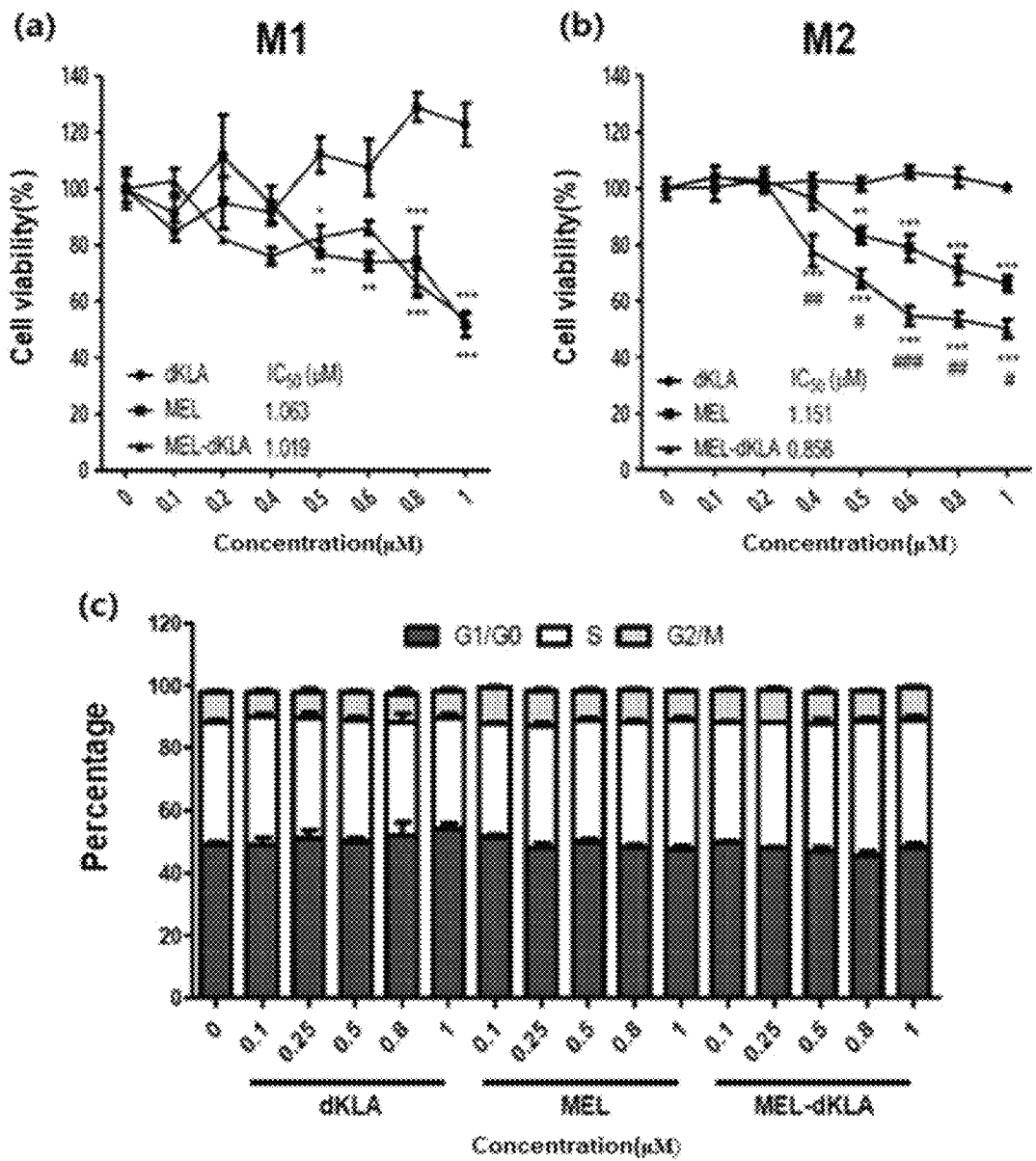
[FIG. 1]

[FIG. 2]
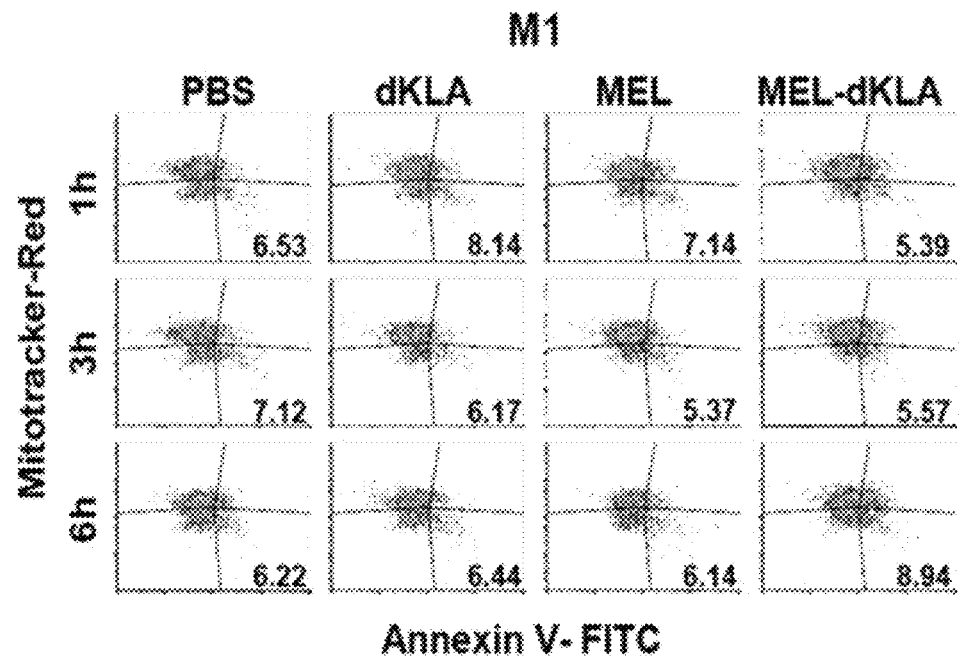
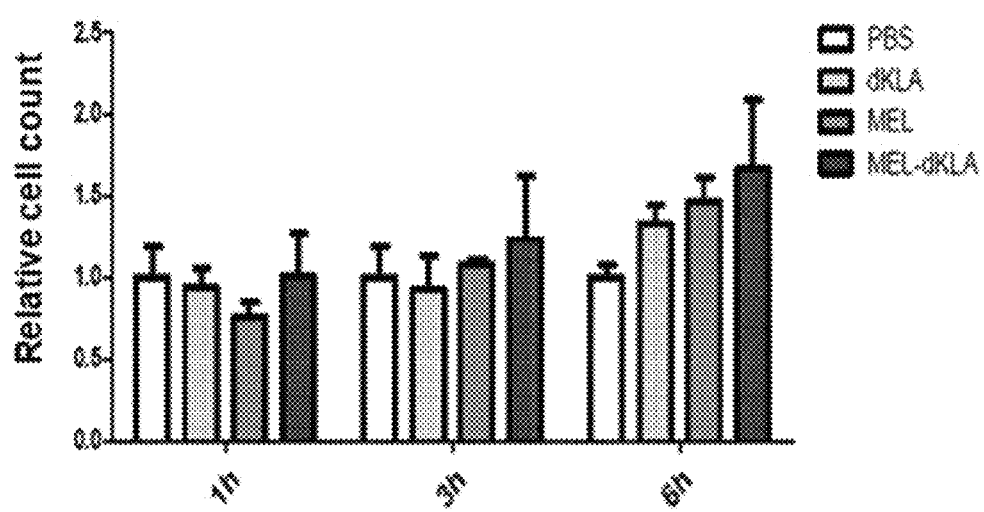

[FIG. 3]
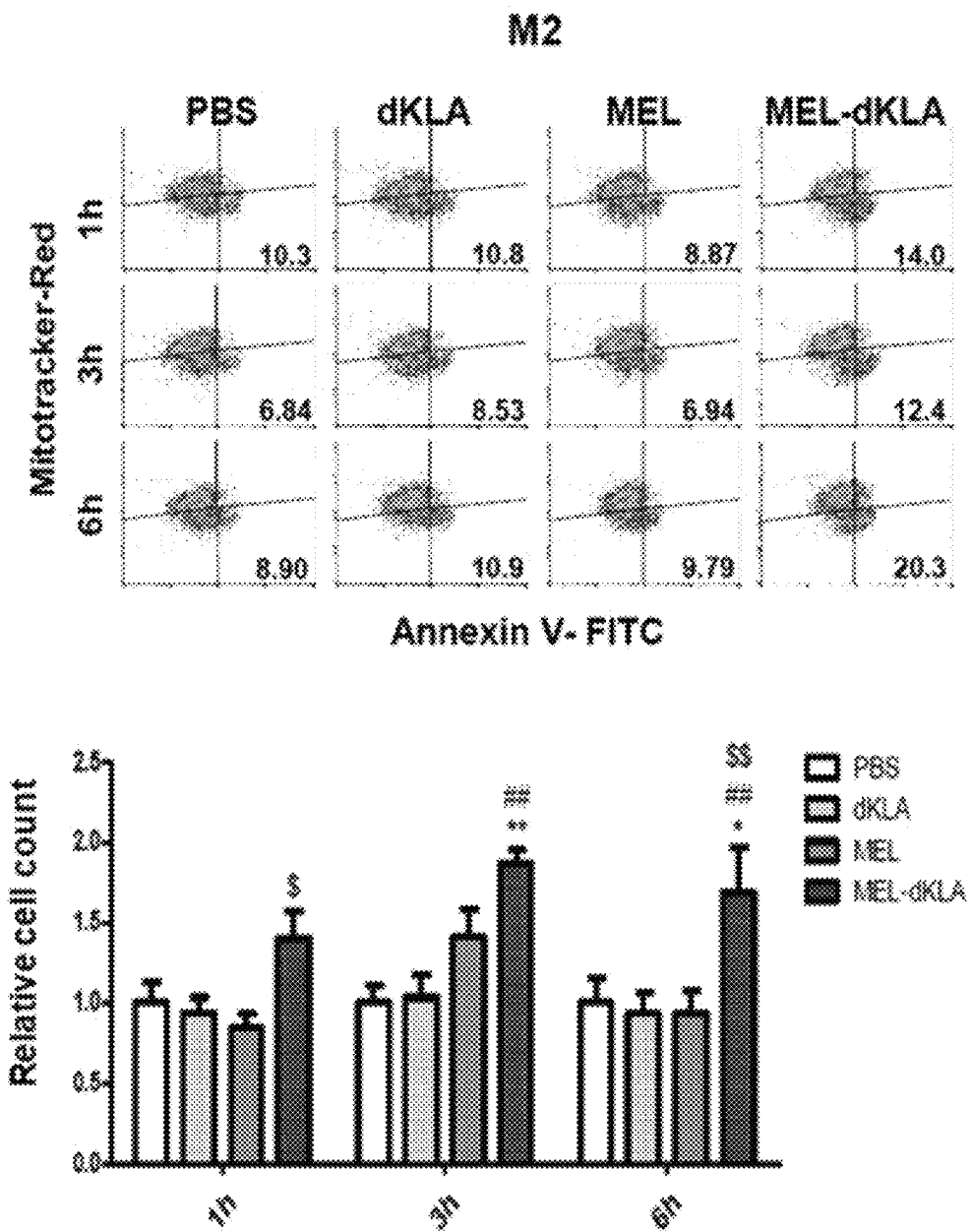

[FIG. 4]
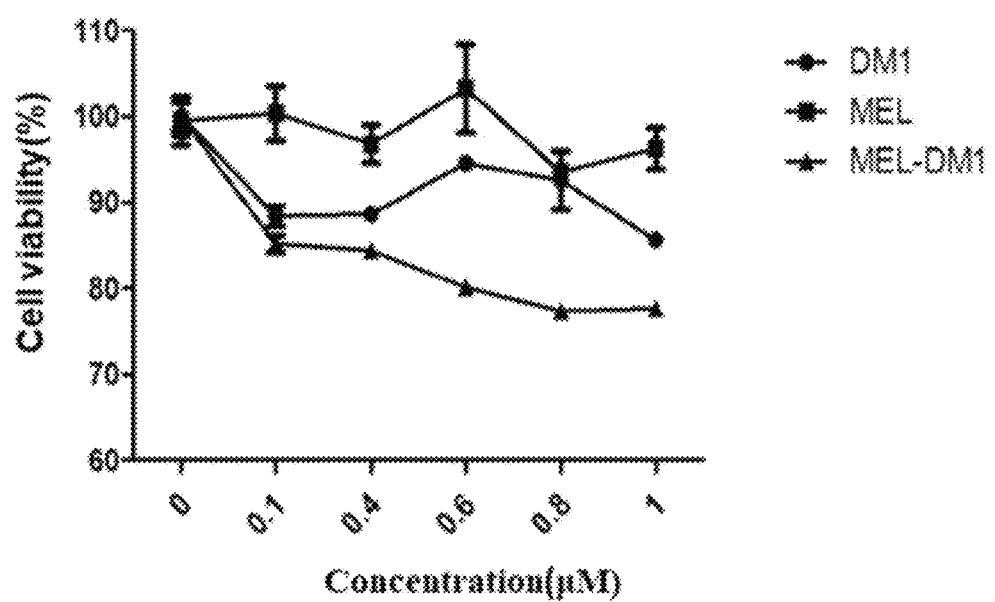

[FIG. 5]
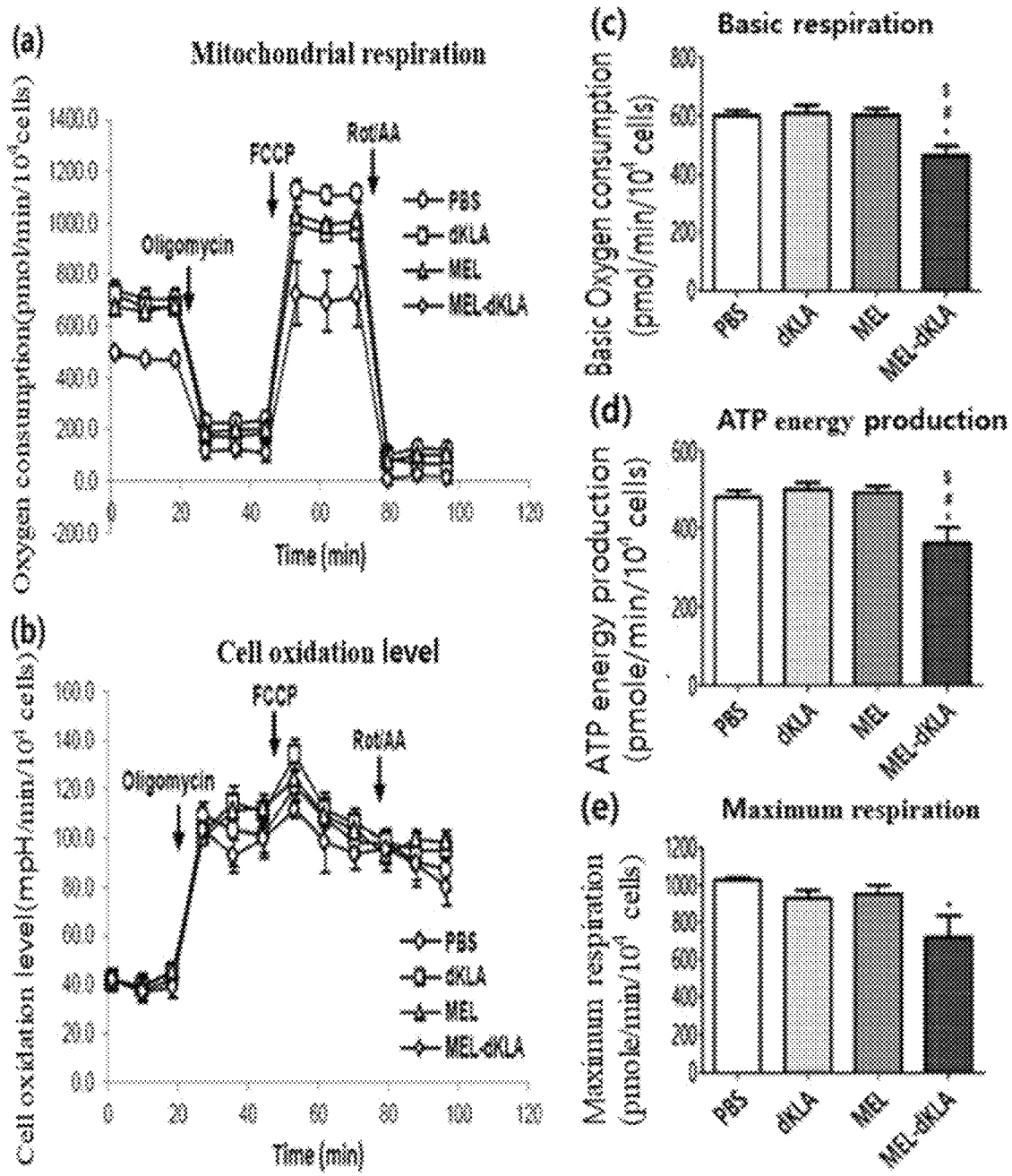

[FIG. 6]
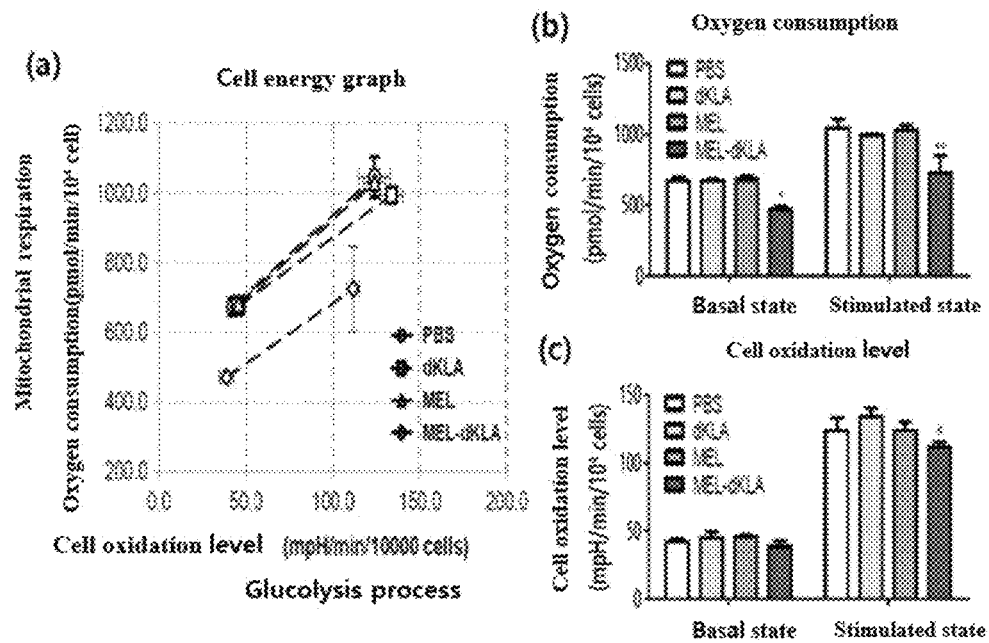

[FIG. 7]
(a)
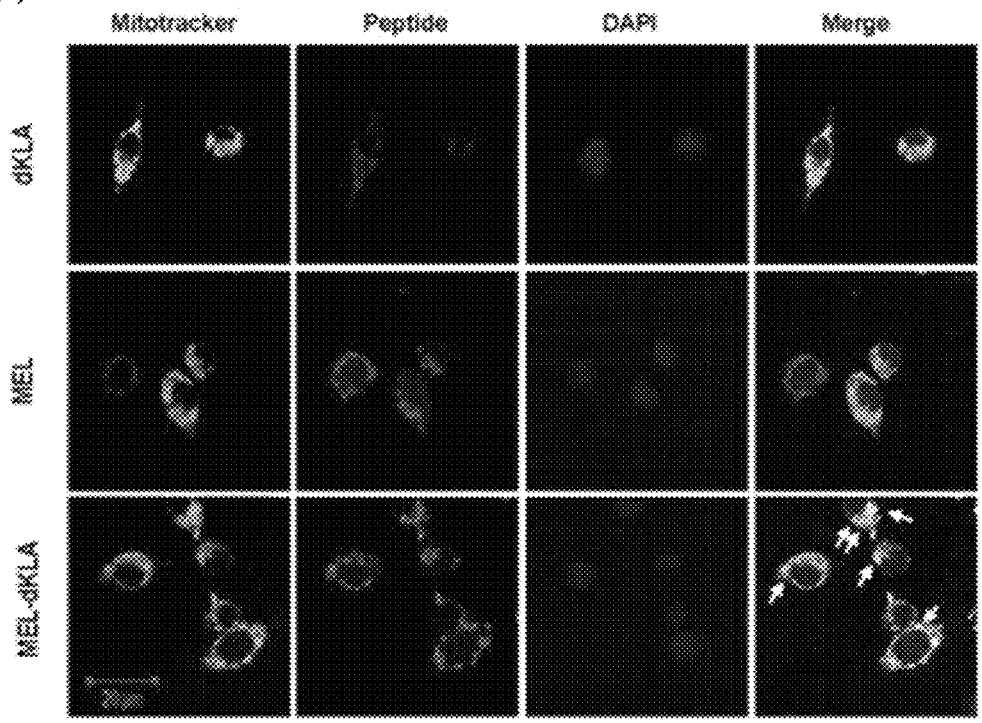
(b)
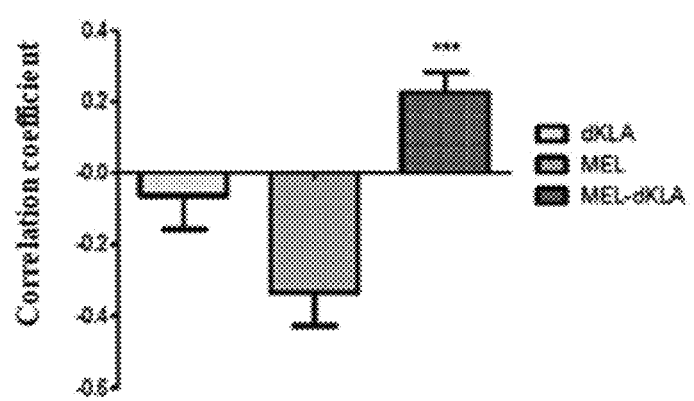

[FIG. 8]
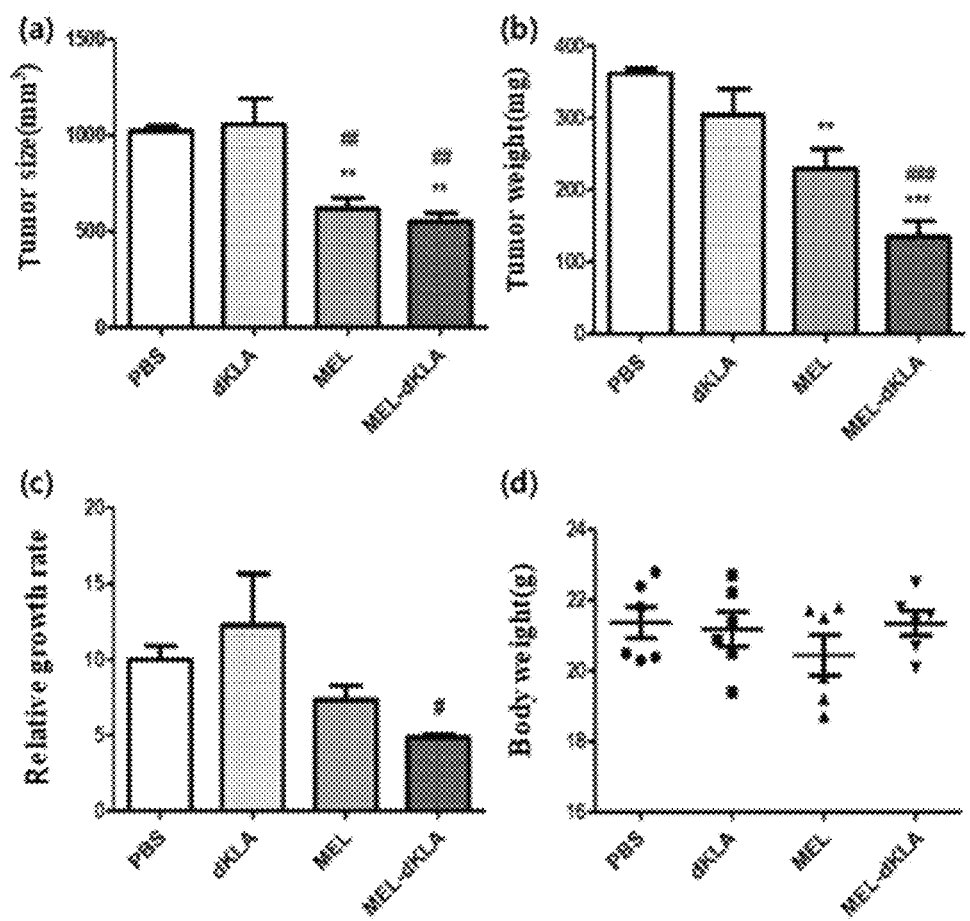

[FIG. 9]
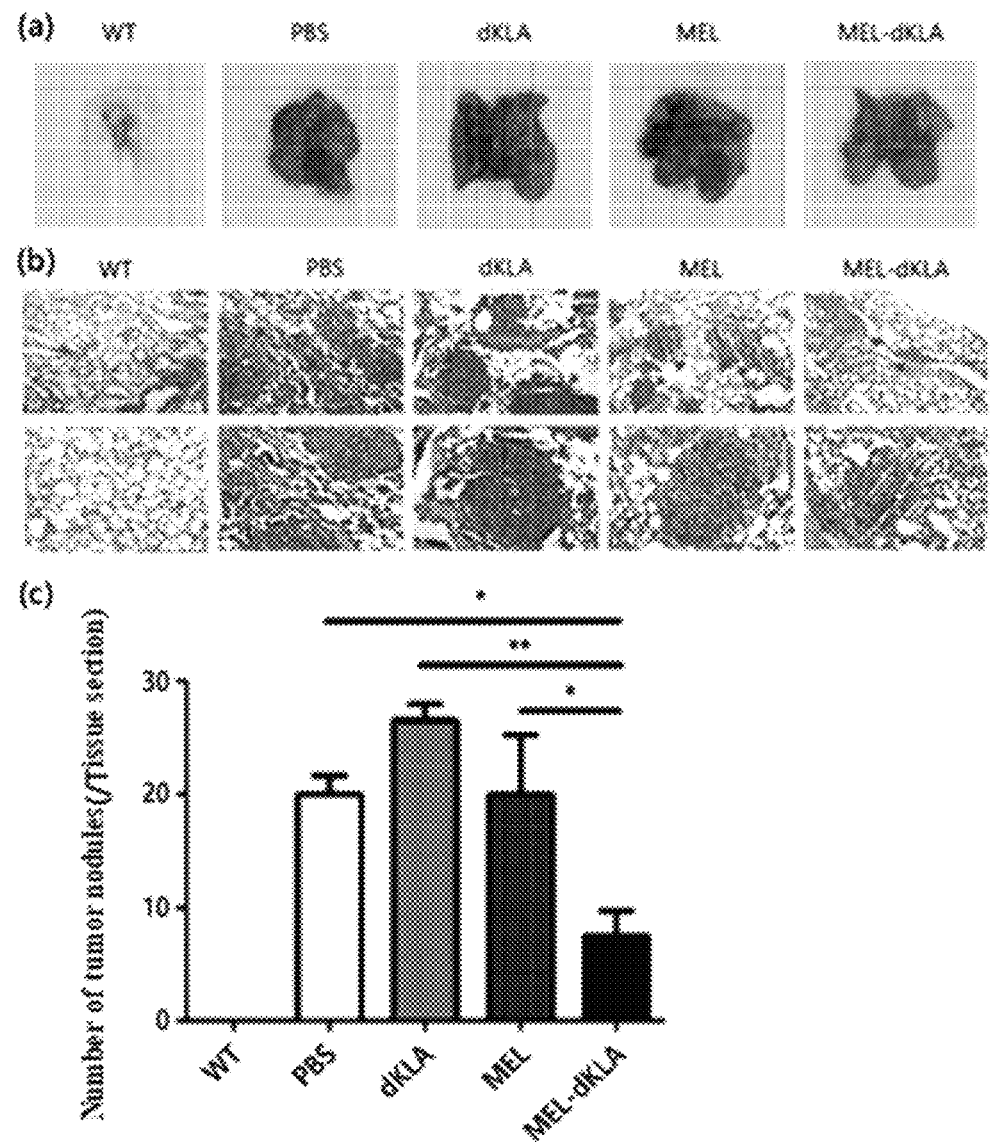

[FIG. 10]
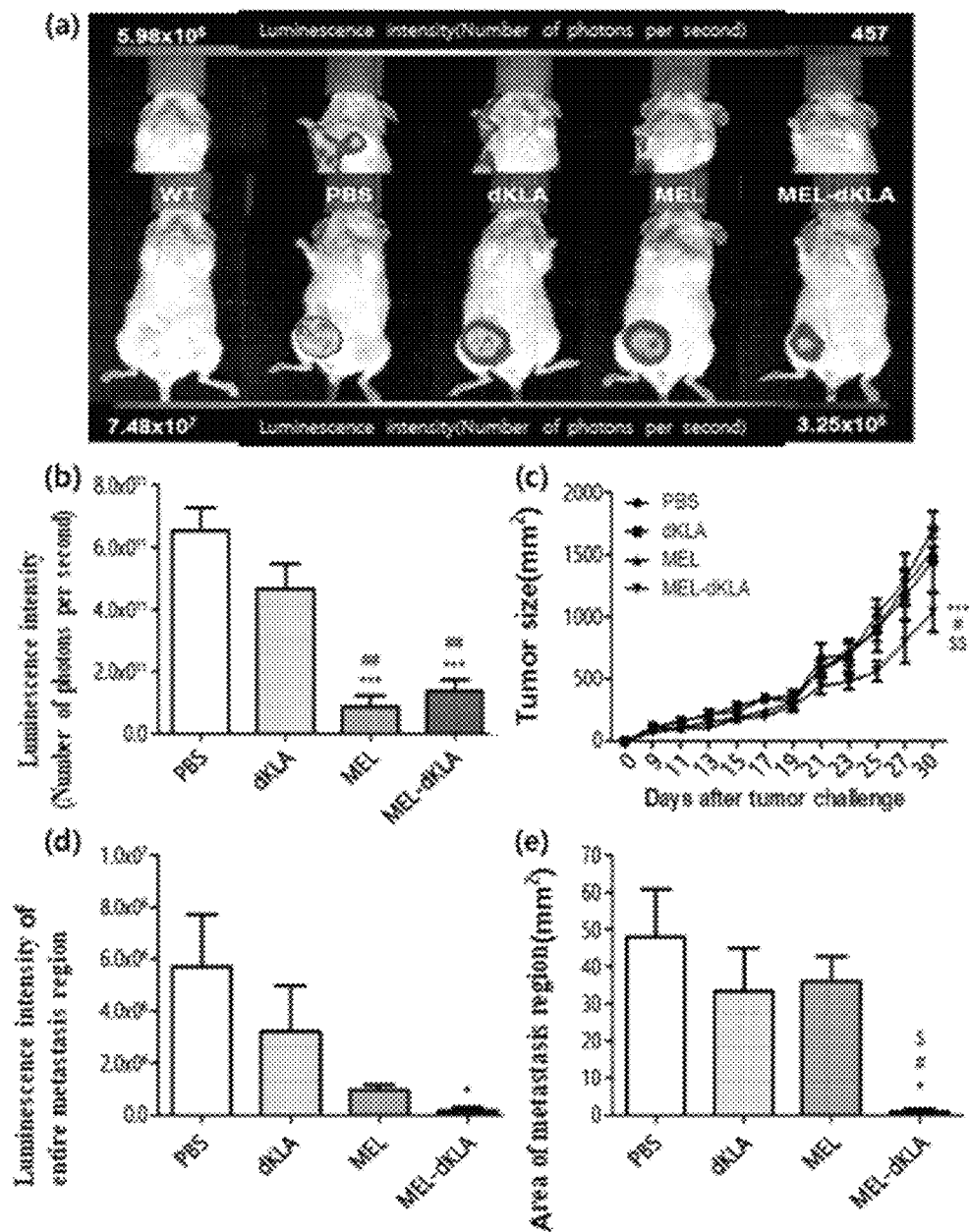

[FIG. 11]
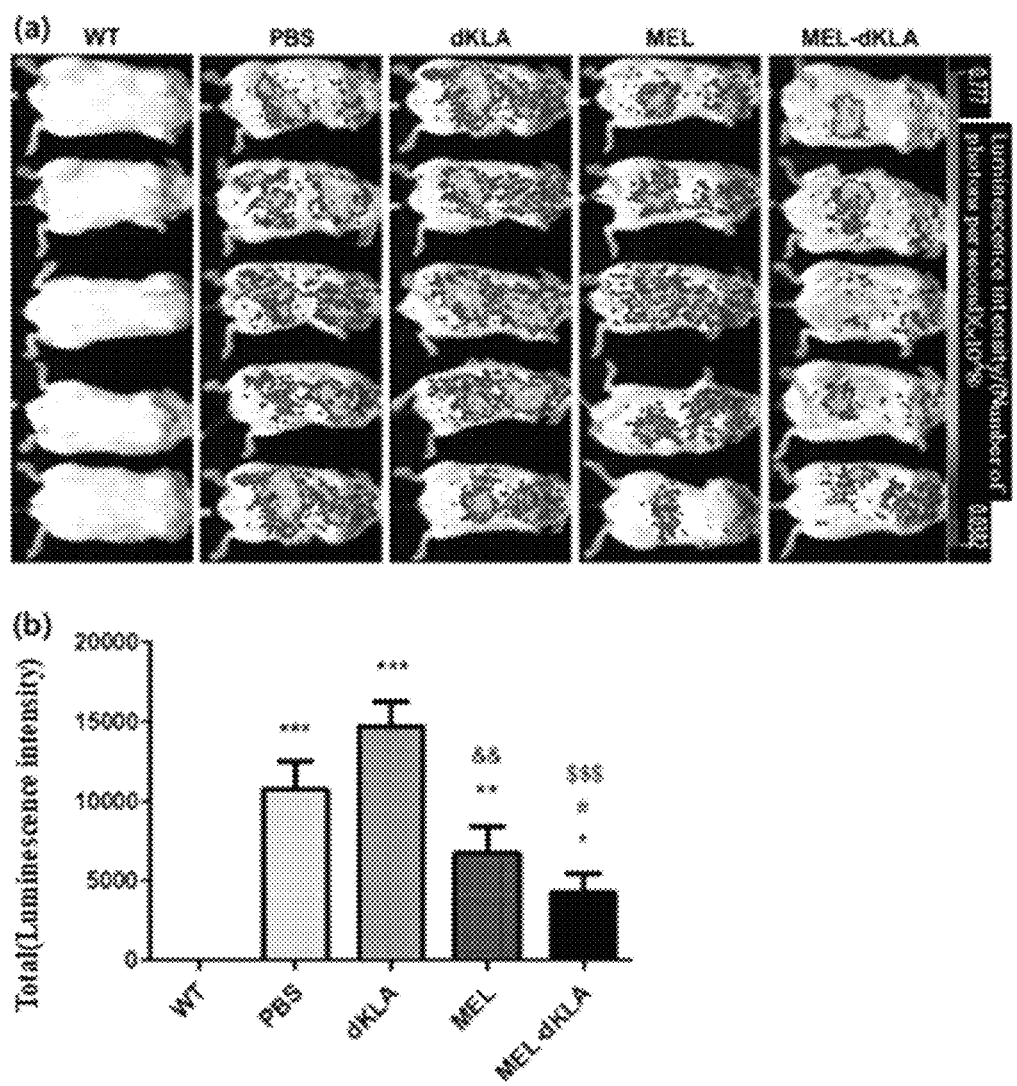

[FIG. 12]
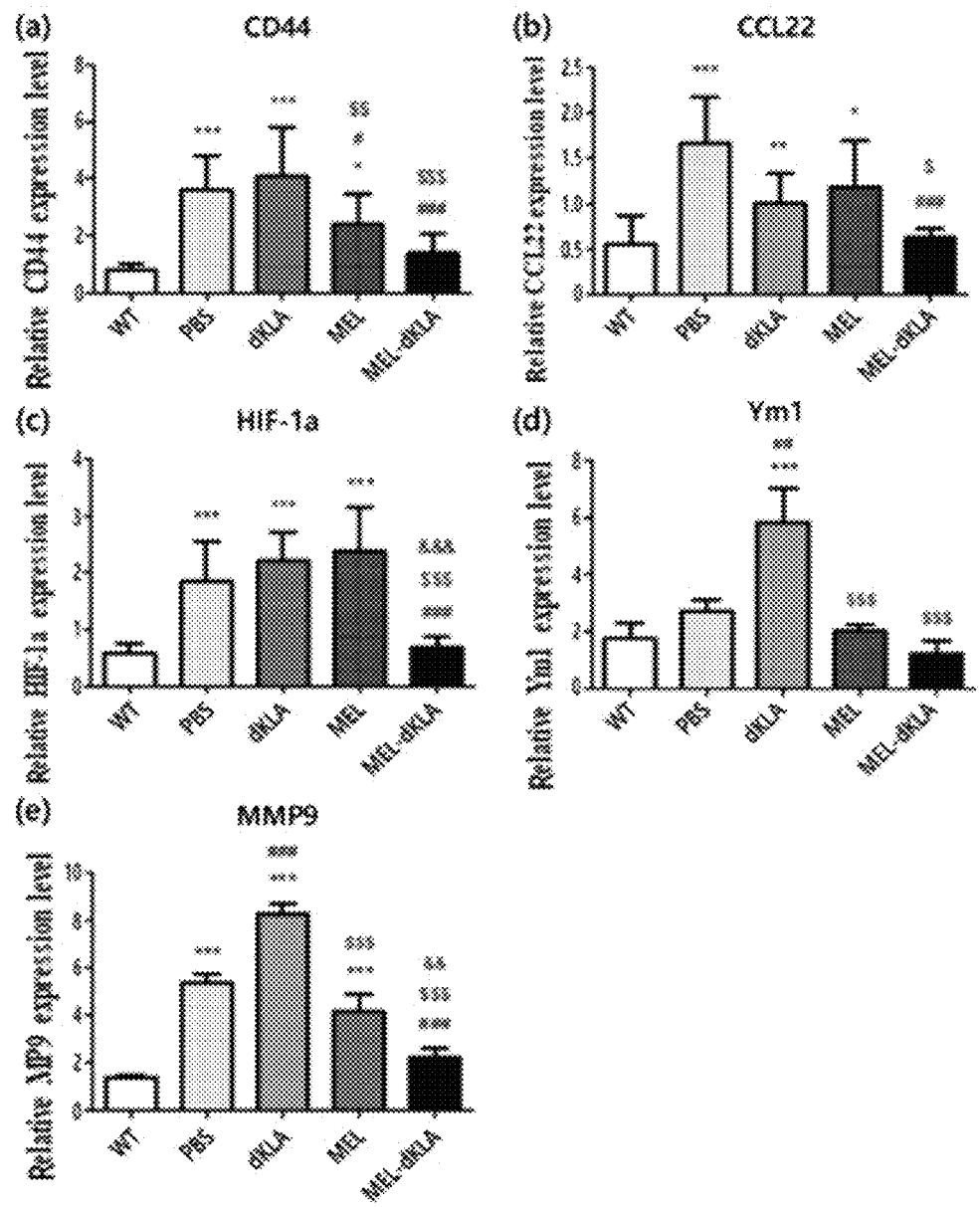

[FIG. 13]
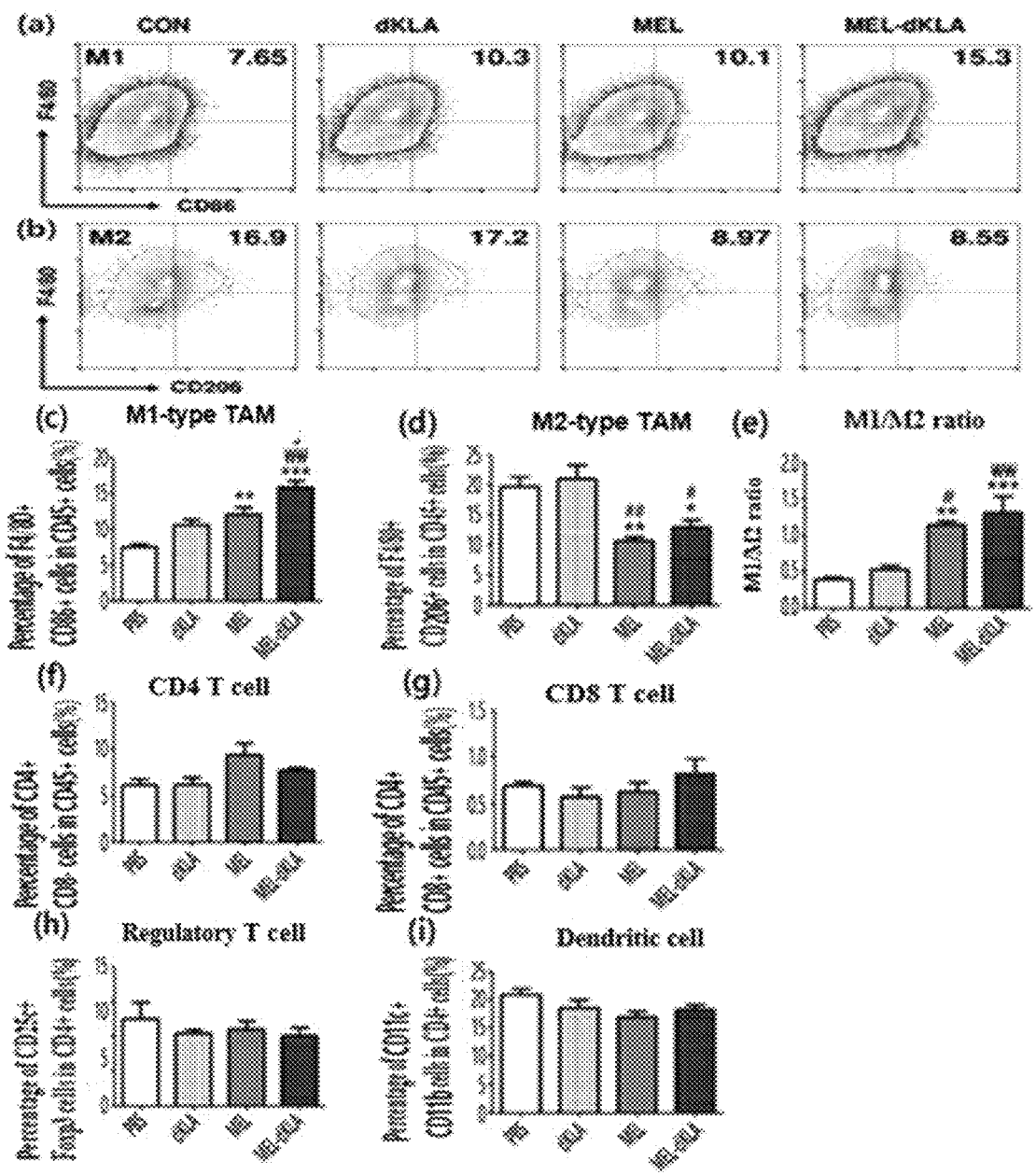

[FIG. 14]
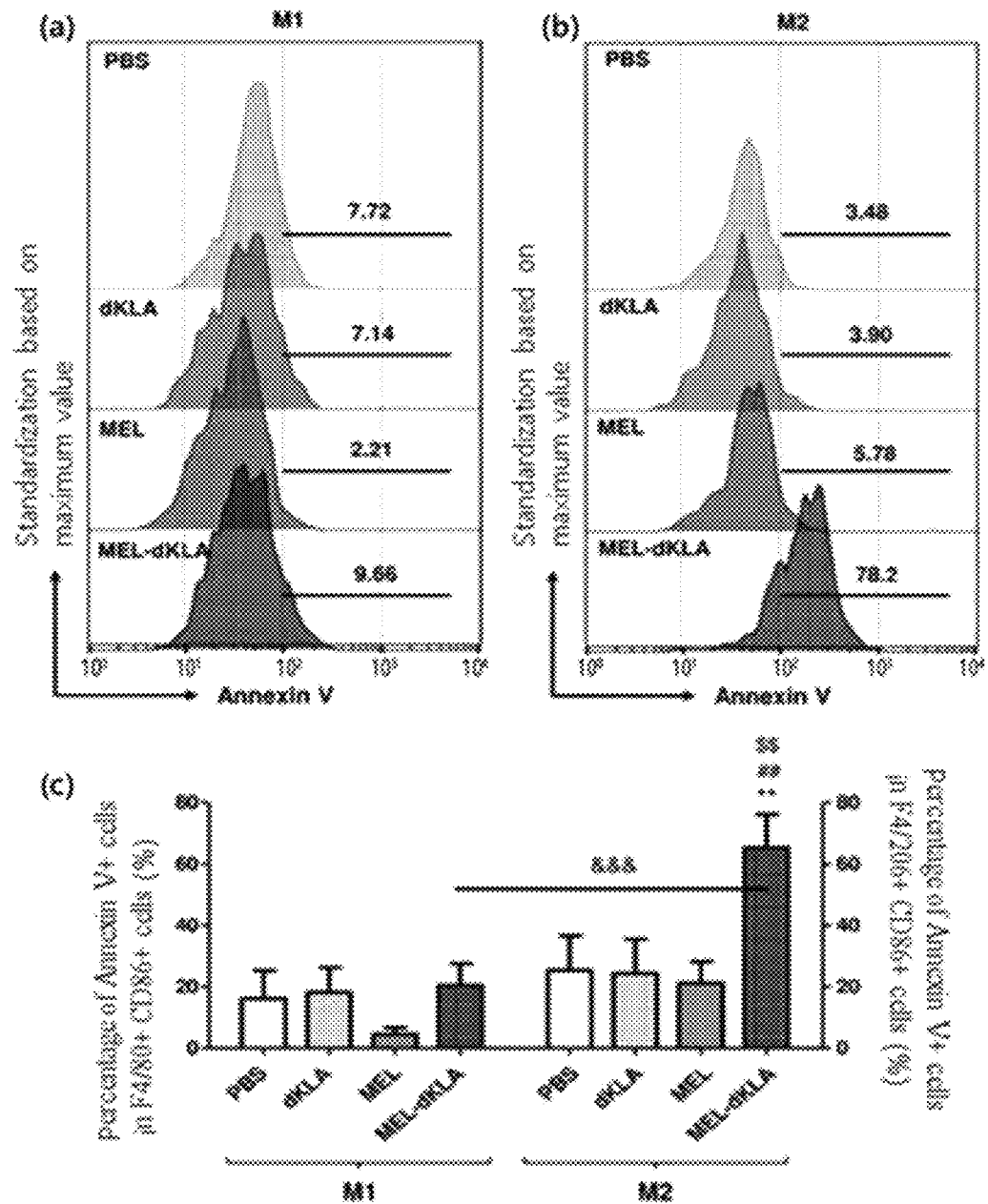

[FIG. 15]
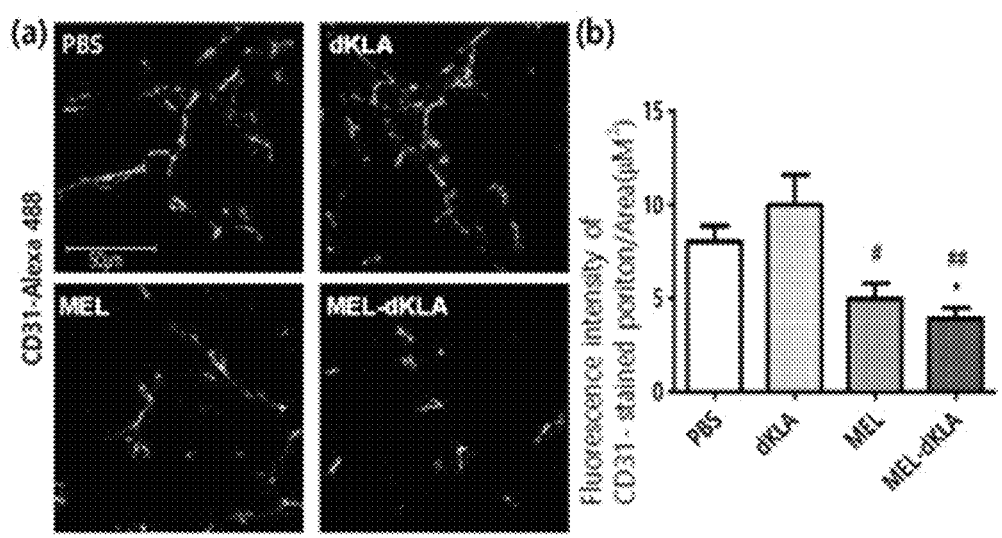

SEQUENCE LISTING

```
<160> NUMBER OF SEQ ID NOS: 13

<210> SEQ ID NO 1
<211> LENGTH: 26
<212> TYPE: PRT
<213> ORGANISM: Artificial Sequence
<220> FEATURE:
<223> OTHER INFORMATION: recombinant peptide

<400> SEQUENCE: 1

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 2
<211> LENGTH: 14
<212> TYPE: PRT
<213> ORGANISM: Artificial Sequence
<220> FEATURE:
<223> OTHER INFORMATION: recombinant peptide

<400> SEQUENCE: 2

Lys Leu Ala Lys Leu Ala Lys Lys Leu Ala Lys Leu Ala Lys
1               5                   10

<210> SEQ ID NO 3
<211> LENGTH: 45
<212> TYPE: PRT
<213> ORGANISM: Artificial Sequence
<220> FEATURE:
<223> OTHER INFORMATION: recombinant peptide

<400> SEQUENCE: 3

Gly Ile Gly Ala Val Leu Lys Val Leu Thr Thr Gly Leu Pro Ala Leu
1               5                   10                  15

Ile Ser Trp Ile Lys Arg Lys Arg Gln Gln Gly Gly Gly Ser Lys
            20                  25                  30

Leu Ala Lys Leu Ala Lys Lys Leu Ala Lys Leu Ala Lys
        35                  40                  45
```

-continued

```
<210> SEQ ID NO 4
<211> LENGTH: 19
<212> TYPE: PRT
<213> ORGANISM: Artificial Sequence
<220> FEATURE:
<223> OTHER INFORMATION: recombinant peptide

<400> SEQUENCE: 4

Thr Gly Gly Ala Thr Cys Cys Gly Ala Ala Thr Thr Ala Gly Cys Thr
1               5                   10                  15

Gly Gly Ala

<210> SEQ ID NO 5
<211> LENGTH: 19
<212> TYPE: PRT
<213> ORGANISM: Artificial Sequence
<220> FEATURE:
<223> OTHER INFORMATION: recombinant peptide

<400> SEQUENCE: 5

Gly Cys Thr Thr Thr Thr Thr Cys Thr Thr Cys Thr Gly Cys Cys Cys
1               5                   10                  15

Ala Cys Ala

<210> SEQ ID NO 6
<211> LENGTH: 19
<212> TYPE: PRT
<213> ORGANISM: Artificial Sequence
<220> FEATURE:
<223> OTHER INFORMATION: recombinant peptide

<400> SEQUENCE: 6

Thr Cys Cys Cys Ala Gly Gly Gly Ala Ala Gly Gly Ala Ala Thr
1               5                   10                  15

Ala Ala Ala

<210> SEQ ID NO 7
<211> LENGTH: 19
<212> TYPE: PRT
<213> ORGANISM: Artificial Sequence
<220> FEATURE:
<223> OTHER INFORMATION: recombinant peptide

<400> SEQUENCE: 7

Gly Gly Thr Thr Thr Gly Gly Ala Thr Cys Ala Ala Gly Cys Cys Cys
1               5                   10                  15

Thr Thr Thr

<210> SEQ ID NO 8
<211> LENGTH: 19
<212> TYPE: PRT
<213> ORGANISM: Artificial Sequence
<220> FEATURE:
<223> OTHER INFORMATION: recombinant peptide

<400> SEQUENCE: 8

Thr Cys Cys Cys Thr Thr Thr Thr Cys Ala Ala Gly Cys Ala Gly
1               5                   10                  15

Cys Ala Gly

<210> SEQ ID NO 9
<211> LENGTH: 19
<212> TYPE: PRT
<213> ORGANISM: Artificial Sequence
```

<220> FEATURE:
<223> OTHER INFORMATION: recombinant peptide

<400> SEQUENCE: 9

Thr Gly Cys Cys Thr Thr Gly Thr Ala Thr Gly Gly Ala Gly Cys
1               5                   10                  15

Ala Thr Thr

<210> SEQ ID NO 10
<211> LENGTH: 23
<212> TYPE: PRT
<213> ORGANISM: Artificial Sequence
<220> FEATURE:
<223> OTHER INFORMATION: recombinant peptide

<400> SEQUENCE: 10

Cys Ala Thr Thr Cys Ala Gly Thr Cys Ala Gly Thr Thr Ala Thr Cys
1               5                   10                  15

Ala Gly Ala Thr Thr Cys Cys
            20

<210> SEQ ID NO 11
<211> LENGTH: 18
<212> TYPE: PRT
<213> ORGANISM: Artificial Sequence
<220> FEATURE:
<223> OTHER INFORMATION: recombinant peptide

<400> SEQUENCE: 11

Ala Gly Thr Gly Ala Gly Thr Ala Gly Cys Ala Gly Cys Cys Thr Thr
1               5                   10                  15

Gly Gly

<210> SEQ ID NO 12
<211> LENGTH: 20
<212> TYPE: PRT
<213> ORGANISM: Artificial Sequence
<220> FEATURE:
<223> OTHER INFORMATION: recombinant peptide

<400> SEQUENCE: 12

Thr Gly Ala Ala Thr Cys Ala Gly Cys Thr Gly Gly Cys Thr Thr Thr
1               5                   10                  15

Thr Gly Thr Gly
            20

<210> SEQ ID NO 13
<211> LENGTH: 20
<212> TYPE: PRT
<213> ORGANISM: Artificial Sequence
<220> FEATURE:
<223> OTHER INFORMATION: recombinant peptide

<400> SEQUENCE: 13

Gly Thr Gly Gly Ala Thr Ala Gly Cys Thr Cys Gly Gly Thr Gly Gly
1               5                   10                  15

Thr Gly Thr Thr
            20

TARGETING M2-LIKE TUMOR-ASSOCIATED MACROPHAGES BY USING MELITTIN-BASED PROAPOPTOTIC PEPTIDE

CROSS REFERENCE TO RELATED APPLICATIONS

This application is a National Stage of International Application No. PCT/KR2019/005438 filed May 7, 2019, claiming priority based on Korean Patent Application No. 10-2018-0051800 filed May 4, 2018, the entire disclosures of which are incorporated herein by reference.

TECHNICAL FIELD

The present disclosure relates to a melittin-anticancer drug conjugate, in which melittin is conjugated with an anticancer drug. More specifically, the present disclosure relates to a melittin-anticancer drug conjugate that inhibits only M2-type tumor-associated macrophage without affecting M1-type tumor-associated macrophage and cancer cells, and a preparation method thereof.

BACKGROUND ART

Tumor-associated macrophages are important innate immune cells found in almost all tissues and originate from the bone marrow and circulate in the blood, and are differentiated in tissues via extravasation. These tumor-associated macrophages are classified into two phenotypes: tumor-suppressing M1 macrophage or tumor-supporting M2 macrophage. M1 macrophage has a strong ability to present antigens, and is generally activated by interferon-γ, lipos-accharide (LPS), and tumor necrosis factor (TNF)-α, and has pro-inflammatory and bactericidal effects.

M2 macrophages are known to promote immunosuppression, tumorigenesis and angiogenesis by releasing various extracellular matrix components, angiogenesis and chemotactic factors. Generally, the M2 macrophages are induced by IL-4 and IL-13, and are distinguished from M1 macrophages in which the M2 macrophages express unique M2 markers such as arginase-1, mannose (MMR, CD206), and scavenger receptors (SR-A, CD204).

Melittin is a major component of bee venom of honeybee (Apis mellifera L.) and is an amphiphilic peptide with 26 amino acid residues. The melittin has membrane-perturbing effects such as pore formation, fusion and vesicle formation. The melittin has been used in tumor-bearing rat studies because of its cell toxicity against tumor cells and its ability to inhibit cell growth or induce cell death and necrosis (Cancer Immunol Immunother. 2004; 53:411-421).

In addition, conventional techniques using melittin are related to a composition for treating arteriosclerosis containing melittin (Korean Patent Application Publication No. 10-2011-0117789), a composition that inhibits the activity of fibroblast-like-synovial cells containing melittin (Korean Patent Application Publication No. 10-2011-0117788) and the like.

Further, a pharmaceutical composition that selectively kills M2-type macrophage using melittin has been identified (Korean Patent Application Publication Number: 10-2019-0021765). However, in this patent document, there is no known description of an M2 targeting pharmaceutical composition which is conjugated with the melittin as a conjugation partner. Therefore, the present inventors prepared a conjugate in which melittin is conjugated with an anticancer drug, and identified that the melittin inhibits only CD206+ tumor-associated macrophage as the M2-type tumor-associated macrophage without affecting CD86+ tumor-associated macrophage as the M1-type tumor-associated macrophage and cancer cells in the tumor mouse model. Thus, we completed the conjugate according to the present disclosure, which significantly reduced side effects caused by the conventional anticancer drugs.

DISCLOSURE

Technical Purpose

A purpose of the present disclosure is to provide a melittin-anticancer drug conjugate in which melittin is conjugated with an anticancer drug.

Another purpose of the present disclosure is to provide a method of preparing the melittin-anticancer drug conjugate by conjugating melittin and anticancer drug to each other.

Technical Solution

One aspect of the present disclosure for achieving the above purpose provides a melittin-anticancer drug conjugate, in which melittin and anticancer drug are conjugated to each other.

The term "melittin (MEL)" in the present disclosure is a peptide that constitutes a main component of bee venom. The term "bee venom (BV)" as used herein is a mixture of acidic and basic secretions produced in the abdomen of bees (Apismellifera) and has a colorless bitter liquid form. Main components thereof are melittin, and apamin as a peptide and mast cell degranulating (MCD) peptides, and phospholipase A2 (PLA2) as an enzyme and the like. In addition, the BV contains various trace amounts of components. Therefore, the melittin of the present invention may be isolated from the bee venom of bees (Apis mellifera). However, the present disclosure is not limited thereto.

In a specific example according to the present disclosure, it was identified that when a conjugate obtained by conjugating an apoptosis peptide dKLA to a MEL peptide targeting CD206+ M2 macrophage via a GGGS linker was applied to M1-type and M2-type macrophages, only M2-type macrophages in a tumor stroma were removed without affecting other eukaryotic cells (FIGS. 1 to 3). It was identified that the conjugate obtained by conjugating the DM1 anticancer drug to the MEL peptide also removed only the M2-type macrophage in the tumor stroma (FIG. 4). A fact that the cell death is due to mitochondria membrane disturbance was identified by measuring cell respiration (FIG. 5 to FIG. 6). It was identified via staining that the conjugate according to the present disclosure was inserted into the mitochondria (FIG. 7). Further, compared to the cases where experimental mice were treated with MEL, dKLA, and MEL-dKLA, an MEL-dKLA conjugate further reduced the size and weight of the tumor (FIG. 8), and also reduced the number of tumor nodules and suppressed intratumor metastasis (FIG. 9). Further, it was identified based on light emission that the conjugate inhibited breast cancer growth in the experimental mice, and inhibited metastasis to the lungs and whole body (FIGS. 10 to 11). Further, we identified that when applying the MEL-anticancer drug conjugate to the animal model, expression of CD44 which is widely expressed in cancer, expression of CCL22, which is known as an M2-type macrophage marker, expression of HIF-1α, which is known as angiogenesis, metastasis, and infiltration marker, expression of Ym1, which is a marker of M2-type macrophage, and expression of MMP-9 involved in the migration and settlement of tumor cells were lowered (FIG. 12). It was identified via staining that the percentage change of immune cells in the tumor was measured to identify that only M2-type TAM decreased (FIG. 13). Selective cell death of M2-type tumor-associated macrophage (TAM) was identified via staining (FIG. 14). Further, it was identified that after treatment with MEL and MEL-dKLA, tumor endothelial cells were confocally photographed to identify a decrease in blood vessel density in endothelial cells (FIG. 15).

The melittin according to the present disclosure serves to target M2-type macrophage, and to deliver the anticancer drug conjugated to the melittin to M2-type macrophage, thereby to exhibit anticancer activity. However, the present disclosure is not limited thereto.

According to the present disclosure, the term "anticancer drug" is a generic term for drugs used in chemotherapy for treating cancer. The anticancer drug may be a compound or pro-apoptotic peptide. However, the present disclosure is not limited thereto.

According to the present disclosure, the term "cancer" refers to a tumor abnormally grown due to the autonomous overgrowth of body tissues, or a disease related to the tumor.

Specifically, the cancer may be lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophageal cancer, gastric cancer (e.g., papillary adenocarcinoma, mucinous adenocarcinoma, adenosquamous carcinoma), duodenal cancer, small intestine cancer, colorectal cancer (e.g. colon cancer, rectal cancer, anal cancer, familial colorectal cancer, hereditary nonpolyposis colorectal cancer, gastrointestinal stromal tumor), breast cancer (e.g., invasive ductal cancer, non-invasive ductal cancer, inflammatory breast cancer), ovarian cancer (e.g., epithelial ovarian carcinoma, extra-testicular germ cell tumor, ovarian germ cell tumor, ovarian low grade serious tumor), testis cancer, prostate cancer (e.g., hormone-dependent prostate cancer, hormone-independent prostate cancer), liver cancer (e.g., hepatocellular carcinoma, primary liver cancer, extrahepatic bile duct cancer), thyroid cancer (e.g., medullary thyroid carcinoma), kidney cancer (e.g., renal cell carcinoma, metastasisal epithelial carcinoma of the kidney and ureter), uterine cancer (e.g., cervical cancer, cervical cancer, uterine sarcoma), brain tumors (e.g., medulloblastoma, glioma, pineal gonadoblastoma, spheroid gonadocytoma, diffuse gonadoblastoma, degenerative gonadoblastoma, pituitary adenoma), retinoblastoma, skin cancer (e.g., basal cell carcinoma, malignant melanoma), sarcoma (e.g., rhabdomyosarcoma, leiomyosarcoma, soft tissue sarcoma), malignant bone tumor, bladder cancer, blood cancer (e.g., multiple myeloma, leukemia, malignant lymphoma, Hodgkin's disease, chronic myeloproliferative disease), primary unknown cancer, etc. More specifically, the cancer may be lung cancer, metastatic cancer or breast cancer. Further specifically, the lung cancer may be Lewis lung cancer. However, the present disclosure is not limited thereto.

According to the present disclosure, the anticancer drugs may be doxorubicin, methotrexate, entinostat, cladribine, pralatrexate, lorlatinib, maytansine DM1, maytansine DM3, and maytansine DM4. However, the present disclosure is not limited thereto.

According to the present disclosure, the term "pro-apoptosis" refers to the process in which the cell leads to death while the cell actively consumes ATP, which is bioenergy.

The typical apoptosis process proceeds via cell shrinkage, regular cleavage of DNA, and fragmentation of cell membranes. Apoptosis may be induced when cells fail to maintain their normal function due to abnormal cell division, radiation, ultraviolet radiation, bacterial infection or viral infection.

According to the present disclosure, the pro-apoptotic peptide may be selected from a group consisting of KLA, alpha-defensin-1, BMAP-28, brevenin-2R, buforin IIb, cecropin A-magainin 2 (CA-MA-2), cecropin A, cecropin B, chrysophsin-1, D-K6L9, gomesin, lactoferricin B, LLL27, LTX-315, magainin 2, magainin II-bombesin conjugate (MG2B), pardaxin and combinations thereof. However, the present disclosure is not limited thereto.

According to the present disclosure, the term "peptide" refers to a polymer composed of amino acids conjugated via an amide bond (or peptide bond). For the purpose of the present disclosure, the peptide has high selectivity to cancer cells, and exhibits strong anticancer activity.

According to the present disclosure, the peptide preferably has the amino acid sequence, but is not limited thereto. According to a preferred embodiment of the present disclosure, the peptide has a content of the amino acid of 50% or greater, preferably 60% or greater, more preferably 70% or greater, more preferably 80% or greater, more preferably, 90% or greater, and most preferably 100%.

According to the present disclosure, the peptide may contain a targeting sequence, a tag, a labeled residue, and an additional amino acid sequence designed for a specific purpose to increase a half-life, or the stability of the peptide. Further, the peptide according to the present disclosure may be conjugated to coupling partners such as effectors, drugs, prodrugs, toxins, peptides, and delivery molecules.

According to the present disclosure, the peptide may be obtained by various methods well known in the art. In detail, the peptide may be prepared using a gene recombination and protein expression system, or by a method of synthesizing the peptide in vitro via chemical synthesis such as peptide synthesis, by a cell-free protein synthesis method, and the like.

According to the present disclosure, the peptide may be prepared in the form of a pharmaceutically acceptable salt. Specifically, the salt may be formed by adding an acid thereto. For example, the salt may be formed by adding the following substances to the peptide: inorganic acids (e.g. hydrochloric acid, hydrobromic acid, phosphoric acid, nitric acid, sulfuric acid, etc.), organic carboxylic acids (e.g. acetic acid, halo acetic acid such as trifluoroacetic acid, propionic acid, maleic acid, succinic acid, malic acid, citric acid, tartaric acid, salicylic acid), acidic sugars (glucuronic acid, galacturonic acid, gluconic acid, ascorbic acid), acidic polysaccharides (e.g., hyaluronic acid, chondroitin sulfate, arginic acid), organic sulfonic acids (e.g., methanesulfonic acid, p-toluene sulfonic acid) including sulfonic acid sugar esters such as chondroitin sulfate, or the like.

The term "conjugate" according to the present disclosure refers to a conjugate in which a melittin peptide and an anticancer drug are conjugated to each other which may target M2-type tumor-associated macrophage. The conjugate may bind to the M2-type macrophage targeted by the drug and damage the mitochondria of the macrophage to inhibit tumor growth and metastasis, and may suppress the cancer by selectively suppressing angiogenesis around the tumor.

That is, the conjugate according to the present disclosure may have improved anticancer activity compared to anticancer drugs. However, the present disclosure is not limited thereto.

According to the present disclosure, the conjugate may be obtained by conjugating a peptide dKLA (SEQ ID NO: 2; d[KLAKLAKKLAKLAK]) to MEL (SEQ ID NO: 1; GIGAVLKVLTTGLPALISWIKRKRQQ) purchased from Piscataway, N.J., USA via a GGGGS linker. Alternatively, the conjugate may be obtained by conjugating anticancer drugs such as doxorubicin, methotrexate, entinostat, cladribine, pralatrexate, and lorlatinib to the MEL via an SPDP linker. Alternatively, the conjugate may be obtained by conjugating maytansine DM1, maytansine DM3 and maytansine DM4 to the MEL without a linker. However, the present disclosure is not limited thereto.

That is, the conjugate according to the present disclosure may be in a form in which melittin is directly conjugated to an anticancer drug or is conjugated thereto via a chemical linker. However, the present disclosure is not limited thereto.

According to the present disclosure, the term "chemical linker" may bind to the drug and the MEL via an amine, carboxyl or sulfhydryl group on melittin and anticancer drug. However, the present disclosure is not limited thereto. Specifically, the chemical linker may be selected from a group consisting of EDC (1-ethyl-3-(3-dimethylaminopropyl)carbodiimide), DCC (N,N'-dicyclohexylcarbodiimide), SATA (succinimidyl acetylthioacetate), sulfo-SMCC (sulfosuccinimidyl-4-(NDmaleimidomethyl)cyclohexane-1-carboxylate), DMA (dimethyl adipimidate.2HCl), DMP (dimethylpimelimidate.2HCl), DMS (dimethyl Suberimidate.2HCl), DTBP (dimethyl 3,3'-dithiobispropionimidate.2HCl), sulfo-SIAB (sulfosuccinimidyl(4-iodoacetyl)aminobenzoate), SIAB (succinimidyl(4-iodoacetyl)aminobenzoate), SBAP (succinimidyl 3-(bromoacetamido)propionate), SIA (succinimidyl iodoacetate), SM(PEG)n (succinimidyl-([N-maleimidopropionamido]-#ethyleneglycol ester, wherein n=2, 4, 6, 8, 12 or 24), SMCC (succinimidyl-4-(N-Dmaleimidomethyl)cyclohexane-1-carboxylate), LCSMCC (succinimidyl 4-(N-maleimidomethyl)cyclohexane-1-carboxy-(6-amidocaproate)), sulfo-EMCS (N-εester), EMCS (N-εsulfo-GMBS(N-γester), GMBS (N-γ ester), sulfo-KMUS (N-κester), sulfo-MBS (m-maleimidobenzoyl-Nhydroxysulfosuccinimide ester), MBS (m-maleimidobenzoyl-N-hydroxysuccinimide ester), sulfo-SMPB (sulfosuccinimidyl 4-(p-maleimidophenyl)butyrate), SMPB (succinimidyl 4-(pmaleimidophenyl)butyrate), AMAS (N-α-maleimidoacet-oxysuccinimide ester), BMPS (N-β-maleimidopropyloxysuccinimide ester), SMPH (succinimidyl 6-[(β-maleimidopropionamido)hexanoate]), PEG12-SPDP (2-pyridyldithiol-tetraoxaoctatriacontane-N-hydroxysuccinimide), PEG4-SPDP, sulfo-LCSPDP (sulfosuccinimidyl6-[3'-(2-pyridyldithio)propionamido]hexanoate), SPDP (succinimidyl 3-(2-pyridyldithio)propionate), LC-SPDP (succinimidyl 6-[3'-(2-pyridyldithio)propionamido]hexanoate), SMPT (4-succinimidyloxycarbonyl-alpha-methyl-alpha(2-pyridyldithio)toluene), DSS (disuccinimidyl suberate), BS(PEG)5 (bis(succinimidyl) penta (ethylene glycol)), BS(PEG)9 (bis(succinimidyl) nona (ethylene glycol)), BS3 (bis[sulfosuccinimidyl] suberate), BSOCOES (bis[2-(succinimidooxycarbonyloxy)ethyl] sulfone), PDPH (3-(2-pyridyldithio)propionyl hydrazide), DSG (disuccinimidyl glutarate), DSP (dithiobis[succinimidyl propionate]), BM(PEG)n (1,8-bismaleimido-ethyleneglycol, n=2 or 3), BMB (1,4-bismaleimidobutane), BMDB (1,4-bismaleimidyl-2,3-dihydroxybutane), BMH (bismaleimidohexane), BMOE (bismaleimidoethane), DTME (dithiobismaleimidoethane), TMEA (tris(2-maleimidoethyl)amine), DSS (disuccinimidyl suberate), DST (disuccinimidyl tartarate), DTSSP (3,3'-dithiobis[sulfosuccinimidylpropionate]), EGS (ethylene glycol bis [succinimidylsuccinate]), sulfo-EGS (ethylene glycol bis [sulfosuccinimidylsuccinate]), TSAT (tris-succinimidyl aminotriacetate), DFDNB (1,5-difluoro-2,4-dinitrobenzene), and combinations thereof. However, the present disclosure is not limited thereto.

The term "tumor-associated macrophage (TAM)" according to the present disclosure refers to a macrophage that plays an important role in the overall tumor microenvironment such as cancer growth and metastasis. The tumor-associated macrophages present around the tumor are closely related to the growth and metastasis of tumor cells. Tumor-associated macrophages are classified into two phenotypes: tumor-suppressing M1 macrophage or tumor-supporting M2 macrophage. M2-type tumor-associated macrophages produce cytokines such as IL-10, TGFβ, and CCL18, which promote cancer growth, and suppress anti-tumor activity of T cells and NK cells via surface receptors. These tumor-associated macrophages (TAM) may be differentiated from monocytes and macrophages originating from bone marrow, yolk sac or extramedullary hematopoiesis. Preferably, TAM may be isolated from the bone marrow. However, the present disclosure is not limited thereto.

Another aspect according to the present disclosure for achieving the above purpose provides a pharmaceutical composition for the prevention or treatment of tumor-associated macrophage-mediated diseases.

According to the present disclosure, the composition may be a pharmaceutical composition for the prevention or treatment of cancer growth and metastasis via removal of M2-type tumor-associated macrophage. However, the present disclosure is not limited thereto.

The term "tumor-associated macrophage" according to the present disclosure is as described above.

The term "prevention" according to the present disclosure refers to any action that inhibits or delays tumor growth and metastasis using the conjugate according to the present disclosure.

The term "treatment" according to the present disclosure refers to any action in which the symptoms of tumor growth and metastasis are reduced or beneficially altered using the conjugate.

According to the present disclosure, the conjugate is preferably used for humans. However, the conjugate may be applied to livestock such as cattle, horses, sheep, pigs, goats, camel, antelope, dog or cat in which inflammatory disease or cancer occurs and the cancer may be suppressed or reduced via administration of the peptide according to the present disclosure thereto.

The route and mode of administration for administering the composition for preventing or treating cancer according to the present disclosure are not particularly limited. As long as the composition may reach a target site, any route and mode of administration may be used. Specifically, the composition may be administered via various routes, that is, orally or parenterally. Non-limiting examples of the route of administration may include ocular, oral, rectal, topical, intravenous, intraperitoneal, intramuscular, intraarterial, transdermal, nasal, or inhalation route. Further, the composition may be administered using any device capable of moving the active substance to the target cell.

According to the present disclosure, the pharmaceutical composition may further contain a pharmaceutically acceptable carrier, excipient or diluent commonly used in the preparation of the pharmaceutical composition. The carrier may include a non-naturally occurring carrier.

According to the present disclosure, the term "pharmaceutically acceptable" means to represent a characteristic that is not toxic to cells or humans exposed to the composition.

More specifically, the pharmaceutical composition may be formulated in a form of oral dosage forms such as powders, granules, tablets, capsules, suspensions, emulsions, syrups, aerosols, etc., external preparations, suppositories, and sterile injectable solutions according to a conventional method. Any formulation may be used as long as it is used for the prevention or treatment of cancer in the art. Thus, the present disclosure is not limited thereto.

The carriers, excipients and diluents that may be contained in the pharmaceutical composition may include, for example, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, polycaprolactone (PCL), poly lactic acid (PLA), poly-L-lactic acid (PLLA), mineral oil, and the like.

The formulation may be prepared using diluents or excipients such as fillers, extenders, conjugation agents, wetting agents, disintegrants, and surfactants which are commonly used.

Solid preparations for oral administration include tablets, pills, powders, granules, capsules, etc. Such solid preparations may be prepared by mixing the composition with at least one excipient such as starch, calcium carbonate, sucrose or lactose, and gelatin. Further, in addition to simple excipients, lubricants such as magnesium stearate and talc may be used.

Liquid preparations for oral administration include suspensions, liquid solutions, emulsions, syrups, etc. In addition to water and liquid paraffin, which are commonly used simple diluents, various excipients, for example, wetting agents, sweeteners, fragrances, preservatives, and the like may be contained in the liquid preparation. Preparations for parenteral administration may include sterilized aqueous solutions, non-aqueous solvent, suspending agent, emulsions, lyophilized preparations, suppositories, and the like. The non-aqueous solvent and suspending agent may include propylene glycol, polyethylene glycol, vegetable oil such as olive oil, and injectable ester such as ethyl oleate. As a base for suppositories, witepsol, macrogol, tween 61, cacao butter, laurin, glycerogelatin, and the like may be used.

Another aspect of the present disclosure for achieving the above purpose provides a method of preparing a melittin-anticancer drug conjugate, the method including conjugating melittin and an anticancer drug to each other.

Another aspect of the present disclosure for achieving the above purpose provides a method of preventing or treating tumor-associated macrophage mediated diseases, the method including administering the conjugate or a pharmaceutical composition containing the same to a subject in need thereof.

Another aspect of the present disclosure for achieving the above purpose provides use of the melittin-anticancer drug conjugate for prevention or treatment of the tumor-associated macrophage-mediated diseases.

Advantageous Effects

The MEL-anticancer drug conjugate according to the present disclosure is an anticancer substance targeting the M2-type tumor-associated macrophage (TAM), and has an excellent effect of selectively selecting the M2-type tumor-associated macrophage (TAM). Thus, the conjugation method between MEL and the anticancer drug may be used for delivery of the drug targeting the M2-type tumor-associated macrophage.

DESCRIPTION OF DRAWINGS

FIG. 1 shows a graph showing the cytotoxicity of dKLA, MEL and MEL-dKLA for M1 via MTS measurement ((a) of FIG. 1), a graph showing the cytotoxicity of dKLA, MEL and MEL-dKLA to M2 via MTS measurement ((b) of FIG. 1), and a graph of analyzing a cell cycle as measured via PI staining ((c) of FIG. 1).

FIG. 2 is a graph showing changes of M1-type macrophage when dKLA, MEL and MEL-dKLA are applied thereto, via staining with Annexin VFITC and MItoTracker-Red CMXRos and via flow cytometry.

FIG. 3 is a graph showing changes of M2-type macrophage when dKLA, MEL and MEL-dKLA are applied thereto, via staining with Annexin VFITC and MItoTracker-Red CMXRos and via flow cytometry.

FIG. 4 is a graph showing the cytotoxicity of MEL-DM1 against M2-type macrophage via MTS measurement.

FIG. 5 shows a graph showing intracellular respiration changes to measure cell death due to mitochondria membrane disturbance ((a) of FIG. 5), a graph showing changes in glycolysis within a cell to measure cell death due to mitochondria membrane disturbance ((b) of FIG. 5), a graph showing changes in basal respiration to measure cell death due to mitochondria membrane disturbance ((c) of FIG. 5), a graph showing changes in cell ATP production to measure cell death due to mitochondria membrane disturbance ((d) of FIG. 5), and a graph showing the maximum respiration change in a cell to measure cell death due to mitochondria membrane disturbance ((e) of FIG. 5).

FIG. 6 shows a graph showing changes in cell energy phenotype as measured using XF to measure cell death due to mitochondria membrane disturbance ((a) of FIG. 6), a graph showing changes in the oxygen consumption rate (OCR) in a cell to measure cell death due to mitochondria membrane disturbance ((b) of FIG. 6), and a graph showing changes in the extracellular acidification rate (ECAR) to measure cell death due to mitochondria membrane disturbance ((c) of FIG. 6).

FIG. 7 shows a stained picture showing the locations of MEL, dKLA and MEL-dKLA in mitochondria ((a) of FIG. 7), and a correlation coefficient of MEL, dKLA and MEL-dKLA in mitochondria ((b) of FIG. 7).

FIG. 8 shows a graph showing tumor size comparison to identify the anticancer effect of MEL-dKLA ((a) of FIG. 8), a graph showing tumor weight comparison to identify the anticancer effect of MEL-dKLA ((b) of FIG. 8), a fold change graph showing tumor size comparison to identify the anticancer effect of MEL-dKLA ((c) of FIG. 8), and a graph showing weight change comparison of mice to identify the anticancer effect of MEL-dKLA ((d) of FIG. 8).

FIG. 9 shows a picture showing the lung comparison of mice to identify the anticancer effects of MEL-dKLA ((a) of FIG. 9), a picture showing the lung comparison of mice via staining to identify the inhibitory effect of MEL-dKLA on cancer metastasis ((b) of FIG. 9), and a graph showing comparison of the number of tumor nodules in the lungs to identify the anticancer effects of MEL-dKLA ((c) of FIG. 9).

FIG. 10 shows a picture showing comparison of cancer growth via injection of luminescent factors in mice to identify the anticancer effect of MEL-dKLA ((a) of FIG. 10), a graph showing comparison of the luminescence intensity in mice to identify the anticancer effect of MEL-dKLA ((b) of FIG. 10), a graph showing comparison of tumor size in mice to identify the anticancer effect of MEL-dKLA ((c) of FIG. 10), a graph showing comparison of the luminescence intensity of the entire metastatic region in mice to identify the anticancer effects of MEL-dKLA ((d) of FIG. 10), and a graph showing comparison of the area of the entire metastatic region in mice to identify the anticancer effects of MEL-dKLA ((e) of FIG. 10).

FIG. 11 shows a picture showing comparison of cancer metastasis via injection of luminescent factors in mice to identify the inhibitory effect of MEL-dKLA on cancer metastasis ((a) of FIG. 11), and a graph showing comparison of the total luminescence intensity in mice to identify the inhibitory effect of MEL-dKLA on cancer metastasis ((b) of FIG. 11).

FIG. 12 shows a graph showing comparison of the expression of CD44 as a cancer expression marker to identify the anticancer effect of MEL-dKLA ((a) of FIG. 12), a graph showing comparison of the expression of CCL22 as an M2-type macrophage marker to identify the anticancer effect of MEL-dKLA ((b) of FIG. 12), a graph showing comparison of the expression of HIF-α known as a metastasis and invasion marker to identify the anticancer effect of MEL-dKLA ((c) of FIG. 12), a graph showing comparison of the expression of Ym1 known as a macrophage marker to identify the anticancer effect of MEL-dKLA ((d) of FIG. 12), and a graph showing comparison of the expression of MMP-9 which is involved in the migration and settlement of tumor cells to identify the anticancer effect of MEL-dKLA ((e) of FIG. 12).

FIG. 13 shows a graph showing the infiltration of M1-type tumor-associated macrophages into the tumor stroma via staining with CD45+F4/80+CD86+ to identify the selective reduction of the M2-type tumor-associated macrophage (TAM) cell count due to treatment with MEL-dKLA ((a) of FIG. 13), a graph showing the infiltration of M2-type tumor-associated macrophages into the tumor stroma via staining with CD45+F4/80+CD206+ to identify the selective reduction of M2-type tumor-associated macrophage (TAM) cell count due to treatment with MEL-dKLA ((b) of FIG. 13), a graph showing percentage of CD45+F4/80+CD86+ of M1-type tumor-associated macrophages invading into the tumor stroma to identify the selective reduction of the M1-type tumor-associated macrophage (TAM) cell count due to treatment with MEL-dKLA ((c) of FIG. 13), a graph showing percentage of CD45+F4/80+CD206+ of M2-type tumor-associated macrophages invading into the tumor stroma to identify the selective reduction of the M2-type tumor-associated macrophage (TAM) cell count due to treatment with MEL-dKLA ((d) of FIG. 13), a graph to identify the M1/M2 ratio change due to treatment with MEL-dKLA ((e) of FIG. 13), a graph to identify changes of CD4 T cells due to treatment with MEL-dKLA ((f) of FIG. 13), a graph to identify changes of CD8 T cells due to treatment with MEL-dKLA ((g) of FIG. 13), a graph to identify changes in regulatory T cells due to treatment with MEL-dKLA ((h) of FIG. 13), and a graph to identify changes in dendritic cells due to treatment with MEL-dKLA ((i) of FIG. 13).

FIG. 14 shows a graph showing M1 via staining to identify the selective cell death of M2-type tumor-associated macrophage (TAM) due to treatment with MEL-dKLA ((a) of FIG. 14), a graph showing M2 via staining to identify the selective cell death of M2-type tumor-associated macrophage (TAM) due to treatment with MEL-dKLA ((b) of FIG. 14), and a graph showing the ratio of stained M1 and M2 to identify the selective cell death of M2-type tumor-associated macrophage (TAM) due to treatment with MEL-dKLA ((c) of FIG. 14).

FIG. 15 shows a picture of an immunofluorescence staining of the endothelial cells of LLC tumors to identify the anti-angiogenic effects of MEL and MEL-dKLA ((a) of FIG. 15), and a graph showing a density of blood vessels per zone to identify the anti-angiogenic effects of MEL and MEL-dKLA ((b) of FIG. 15).

MODES OF THE INVENTION

Preparation Example 1

Conjugation Between MEL and Various Anticancer Drugs 1-1. MEL-dKLA Conjugate

In order to identify the easiness of conjugation between MEL and various anticancer drugs, conjugation of dKLA thereto was performed.

Since MEL (SEQ ID NO: 1) and dKLA (SEQ ID NO: 2) correspond to short peptides, they may be conjugated to each other via amide conjugation between the peptides. At this time, in order to minimize the interaction and fold between MEL and dKLA, a linker composed of 4 glycines and 1 serine was placed therebetween to distinguish both ends from each other. KLA employed a D-type isomer rather than an L-type isomer to minimize degradation in the body.

1-2. MEL-DM1 Conjugate

Conjugation of MEL with DM1 was performed to identify the easiness of conjugation between MEL and various anticancer drugs.

More specifically, melittin in which a maleimide structure is synthesized at the N-terminus of the amino acid sequence was purchased. Maleimide may form a covalent bond with the free-sulfhydryl group (—SH) which DM1 has. After reacting melittin and DM1 with each other in boric acid buffer for 2 hours, buffer non-exchanged and unconjugated melittin were filtered out with PBS using amicon ultra centrifugal filters (Merk Millipore). The melittin has a molecular weight of about 3 kDa. When DM1 is conjugated thereto, the conjugate has a molecular weight of 3.6 kDa or greater. The filter as used was to filter out substance of 3 kDa or greater, and thus isolated the melittin conjugated with DM1. The conjugate was identified using Q-TOF mass spectrometry.

Example 1-1

Delivery of Peptide dKLA Causing Apoptosis to M2-Type Macrophage Via MEL

To investigate whether MEL-dKLA induces apoptosis of M2 macrophage, cell viability was measured at various doses of dKLA, MEL and MEL-dKLA (0.1 to 1 μM).

More specifically, dKLA (SEQ ID NO: 2), MEL (SEQ ID NO: 1), MEL-dKLA (SEQ ID NO: 3; GIGAVLKVLTTGL-PALISWIKRKRQQGGGGS-d[KLAKLAKKLAKLAK]) peptide and 5-carboxyl tetramethylrhodamine (TMR)-conjugated dKLA, MEL and MEL-KLA peptides were purchased from GenScript (Piscataway, N.J., USA). TMR was conjugated with the amino group located at the N-terminal of the peptide. Regarding all of the peptides, 95% or greater purified peptides were used. Murine Lewis lung carcinoma (LLC) cells and macrophage RAW264.7 of mice were cultured in Dulbecco's modified Eagle's medium (DMEM; Welgene, Korea) to which 10% heat-inactivated fetal bovine serum (Welgene), 100 U/mL penicillin and 100 μg/mL streptomycin (Invitrogen, CA, USA) were added. Macrophage (RAW264.7) differentiated into M2-type was treated with IL-4 and IL-13 in the medium for 24 hours. After the treatment, the cells were cultured in a state in which serum was insufficient for 48 hours. M1-type macrophage was treated with 1 ng/mL of LPS for 24 hours to induce differentiation.

The cell viability test was measured via the MTS assay. RAW264.7 macrophage was differentiated into M1-type or M2-type macrophage which was inoculated onto a 96-well plate at 3×10$^4$ cells/well. The next day, the macrophage was treated with each of PBS, dKLA, MEL and MEL-dKLA. After 24 hours, the culture solution was replaced and the cell was treated with 20 μL MTS reaction solution (Promega, WI, USA), followed by reaction at 37° C. Then, fluorescence was measured at 490 nm to measure cell viability.

As a result, as shown in FIG. 1, dKLA was used as a control because it cannot disturb the eukaryotic membrane. Cell viability decreased by about 55 to 53% when the cells were treated with 0.6 to 0.5 μM MEL-dKLA and 79 to 71% MEL, followed by reaction for 24 hours. The half-maximal inhibitory concentration (IC50) of MEL-dKLA against M2 macrophage was lower than that when MEL was used alone (0.85 μM MEL-dKLA/0.6-0.8 μM MEL). However, the viability of M1 macrophage was 86 to 66% when treated with 0.6 to 0.8 μM MEL-dKLA. The viability of M1 macrophage was 74% when treated with 0.6 to 0.8 μM MEL. Therefore, it was identified that there was no significant difference in the IC50 test between the two substances, that is, MEL and MEL-dKLA against the macrophage ((a) and (b) of FIG. 1).

Further, in order to investigate whether MEL-dKLA causes random death of tumor cells, the cell cycle was investigated via PI staining in vitro.

More specifically, cells were fixed with 70% cold ethanol and stored at 20° C. for 24 hours. Then, propidium iodide (PI) was added to PBS containing 0.1% Triton X-100 and 20 μg/ml RNase such that 50 μg/ml concentration was achieved. The mixture was applied to the cell. Measurement was done using a flow cytometry method.

As a result, 0.1 to 1 μM MEL-dKLA did not exhibit cytotoxicity against LLC tumor cells ((c) of FIG. 1).

Example 1-2

Apoptosis of M2 Macrophage Via Mitochondria Membrane Disturbance by MEL-dKLA

Flow cytometry was performed to identify whether M2 macrophage death was caused by disturbance of the mitochondria membrane as caused due to treatment with MEL-dKLA.

More specifically, the cells were stained with Annexin V-fluorescein isothiocyanate (FITC; BD Biosciences, CA, USA) and MitoTracker RedBOX (Invitrogen). The cells were inoculated at 5×10$^5$ cells/well, onto a 24-well plate. The next day, 0.8 μM peptide was applied thereto. In 1, 3 and 6 hours after the application, the cells were reacted with 250 nM MitoTracker for 1 hour in a serum-free culture solution. Thereafter, the cells were collected and reacted with Annexin V again. The reacted cells were measured with BD FACSCalibur, and were analyzed via FlowJo software (Treestar, Inc., CA, USA). MitoTracker could pass through protoplasmic membrane depending on the membrane charge and then accumulated within the mitochondria. In other words, staining may be identified in the mitochondria membrane of living cells, but staining may be difficult in cells where apoptosis occurs due to membrane disturbance.

As a result, as may be seen in FIGS. 2 to 3, when M1 macrophage was treated with MEL and MEL-dKLA peptides for 1 to 3 hours, the effect did not appear. When M1 macrophage was treated therewith for 6 hours, MitoTracker staining was lowered and Annexin V+ staining was increased, but there was no significant change (FIG. 2). However, it was identified that when M2 macrophage was treated with MEL-dKLA for 6 hours, a significant number of cells died. On the contrary, when each of MEL and dKLA was used alone, no significant difference was found (FIG. 3).

Example 1-3

Delivery of Anticancer Drug DM1 That Causes Apoptosis to M2-Type Macrophage Via MEL To investigate whether MEL-DM1 induces apoptosis of M2 macrophage, the cells were treated with DM1, MEL, and MEL-DM1 and then the cell viability was measured.

The MEL-DM1 anticancer drug conjugation method and cell test method are as described above.

As a result, as shown in FIG. 4, treatment with the MEL-DM1 conjugate realized a higher M2 selective cell killing effect than that when treatment each of MEL and DM1 alone. Thus, it was identified that the MEL-anticancer drug conjugate exhibited a better effect.

Example 2

Measurement of Metabolic Change Due to Treatment With MEL-dKLA

Hippocampus assay was performed to measure the effect of MEL-dKLA on the metabolic action of mitochondria.

More specifically, the metabolic action was measured using an XF24 Extracellular Flux analyzer (Agilent, CA, USA). RAW264.7 cells were differentiated into M2 cells which were inoculated into XF-24 plates (3×10$^4$ cells/well). The next day, in order to minimize the potential stress due to changes in the situation, 1 μM of each peptide was added thereto. Then, the cells were incubated in a 37° C. incubator under 5% $CO_2$ condition. After the incubation for a while, we inoculated the cells into 500 μL of XF running culture solution (pH 7.4) containing 4500 mg/L of D-glucose (w/v), 1 mM sodium pyruvate, and 4 mM L-glutamine. Then, the cells were cultured in 37° C. environment without carbon dioxide. Metabolic toxins (1 μM oligomycin, 0.5 μM carbonyl cyanide p-trifluoromethoxy-phenylhydrazone [FCCP], 0.5 μM rotenone and antimycin A [Rot/AA]) were loaded into a drug pot. Then, we added a drug thereto. Then, the oxygen consumption rate (OCR) and the extracellular acidification rate (ECAR) were measured in real time.

Further, OCR was measured at a time point corresponding to 12 times. The basal state was measured at a time point corresponding to 3 times. Then, ATP-connected respiration after oligomycin addition was measured at a time point corresponding to further 3 times. Then, the maximum respiration after FCCP addition was measured at a time point corresponding to further 3 times. Then, a point at which non-mitochondrial respiration occurred after addition of Rot/AA was measured at a time point corresponding to remaining 3 times. Thus, the mitochondria respiration ability was measured. ECAR indicating the glycolysis rate was measured at the same time points.

As a result, as may be seen in FIGS. 5 to 6, the basal respiration of the MEL-dKLA-treated group was significantly lower than that of the PBS-treated group. However, when the cells were treated with dKLA or MEL alone, there was no change in baseline OCR compared to a PBS-treated group ((a) and (b) of FIG. 5). Further, treatment with MEL-dKLA significantly reduced ATP production ((a) and (d) of FIG. 5). Moreover, when the cells were treated with MEL-dKLA, the maximum respiration was significantly lowered ((a) and (e) of FIG. 5). The basal glycolysis ability did not exhibit any significant change. Treatment with oligomycin increased the basal glycolysis ability in all groups ((b) of FIG. 5). It was identified that regarding an energy standard type, treatment with MEL-dKLA decreased respiration capacity in both the basal state and the stress state ((a) and (b) of FIG. 6). However, the baseline ECAR was not suppressed due to treatment with MEL-dKLA, whereas, in the group under stress, ECAR decreased slightly due to treatment with MEL-dKLA, compared to the dKLA-treated group. However, there was no significant difference thereof between the PBS-treated group and the MEL-dKLA-treated group ((a) and (c) of FIG. 6.

Thus, it was identified that the effect of MEL-dKLA was insignificant in the glycolysis of the cytoplasm. Therefore, it was found that the dysfunction of mitochondria respiration was caused due to treatment with MEL-dKLA targeting the mitochondria.

Example 3

Measurement of Selective Invasion of MEL-dKLA Into Mitochondria

In order to identify the invasion and location of MEL-dKLA into the mitochondria of M2-type macrophage, those were identified using fluorescence microscopy via staining. Further, PASCAL 5 LSM image measurement was performed for quantitative analysis.

More specifically, RAW264.7 macrophage was differentiated into M2 which in turn was incubated together with 1 μM TMR-conjugated dKLA, MEL or MEL-dKLA for 2 hours. The peptides that were not conjugated thereto were washed off, and then the cells were stained with 250 nM MitoTracker green (Invitrogen) for 30 minutes. After the staining, the cells were stained for 10 minutes in PBS to which 4 μg/mL 4'6-diamidino-2-phenylidole (DAPI; Sigma-Aldrich, MO, USA) was added. The stained cells were measured with a laser scanning confocal microscope (Carl Zeiss, Germany). The location of MEL-dKLA in the mitochondria was measured with an LSMS image meter (Carl Zeiss).

As a result, as may be seen in FIG. 7, it was identified via the image measurement that MEL-dKLA significantly existed in the mitochondria. However, the MEL could not be identified therein. Further, it was identified that a small amount of dKLA was coupled to the cells ((a) of FIG. 7). Further, only MEL-dKLA exhibited a positive correlation with mitochondria. Each of dKLA and MEL did not have any association with mitochondria ((b) of FIG. 7).

Thus, it was identified that MEL-dKLA selectively reacted with mitochondria and infiltrated into mitochondria.

Example 4

Measurement of Effect of MEL-dKLA on Inhibition of Tumor Cell Growth in Mice

Example 4-1

Measurement of Inhibitory Effect of MEL-dKLA on Lung Cancer Cells in Mice

To identify the anticancer effects of MEL-dKLA and MEL in vivo, tumor changes were identified after injecting PBS, dKLA, MEL, or MEL-dKLA peptide into mice with lung cancer cells.

More specifically, C57BL/6 wild-type mice were purchased from DBL (Korea). LLC tumor cells were mixed with Matrigel (Corning, NY, USA) and then the mixture was injected into the right flank of mice ($5\times10^4$ cells/mouse). Five days after tumor cell injection, the recombinant dKLA, MEL, and MEL-dKLA peptides were injected intraperitoneally thereto for 3 days for a total of three times (175 nmol/kg dosage/weight per each time). All tumor tissues were harvested 12 days after the injection. The animal experiment was approved by the Animal Management Committee of Kyunghee University [KHUASP(SE)-17-087]. The animals were managed via autonomous feeding of water and food under a 12-hour light/dark cycle environment without pathogens.

As a result, as may be seen in FIG. 8, it was identified that in the mice injected with each of PBS and dKLA, tumor steadily grew. MEL-dKLA injection significantly inhibited tumor growth compared to the control group injected with PBS. Further, it was identified that when compared with the group injected with dKLA, the size and weight of the tumor were significantly reduced in the group treated with the MEL-dKLA ((a) and (b) of FIG. 8). Further, it was also identified that the tumor size was significantly reduced even in the group injected with MEL. Importantly, the MEL-dKLA-administered group exhibited a significant reduction in tumor size and weight compared to the dKLA-treated group ((c) of FIG. 8). On the contrary, it was identified that the weight of the mouse did not change in all groups ((d) of FIG. 8).

Thus, it was identified that the MEL-dKLA inhibited tumor growth and metastasis in lung cancer superiorly, compared to treatment with other peptides and treatment with the anticancer drug alone.

Example 4-2

Measurement of the Inhibitory Effect of MEL-dKLA on Breast Cancer Cells in Mice

To determine the tumor suppression and cancer metastasis inhibitory effects of MEL-dKLA and MEL, the tumor was identified, and the level of metastasis thereof to the lungs was identified via staining.

More specifically, 4T1 breast cancer cells ($1\times10^5$) were injected into BALB/c mice. Then, 3 days later, 175 nmol/kg of each of PBS, dKLA, MEL and MEL-dKLA was injected into each group at 3-day intervals. To investigate the level of metastasis and nodules on the lung surface, on 15 days after cancer cell injection, mice were sacrificed and the nodules on the lung surface were identified.

As a result, as shown in FIG. 9, it was identified that nodules on the lung surface were significantly reduced in the group treated with MEL-dKLA, but no reduction thereof was observed in the group treated with each of MEL and dKLA alone ((a) of FIG. 9).

Further, we performed H&E staining via a conventional method. Thus, the level of metastasis to the lung was measured.

More specifically, for H&E staining, we immersed the tissue in a hematoxylin solution, stained the cell nucleus with a purple color. Then, we removed a remaining-stained portion except for the nucleus with an acidic alcohol solution, and immersed the tissue again in an eosin-added solution to stain the cytoplasm with a pink color. Then, the structure of the cell was observed.

As a result, as shown in FIG. 9, it was identified that in the group treated with each of PBS and dKLA alone, tumor cells were widely spread and metastasis occurred. On the contrary, it was identified that relatively smaller metastasis occurred in the group treated with each of MEL and MEL-dKLA ((b) of FIG. 9). MEL-dKLA significantly reduced the number of nodules. However, when MEL was applied alone, there was no significant decrease in the number of nodules ((c) of FIG. 9).

Further, we injected a fluorescent substance 4T1-luciferase into mice. Then, the effect of MEL-dKLA on tumor growth and metastasis was identified via fluorescence.

More specifically, to identify the effect of MEL-dKLA on tumor growth and metastasis when breast cancer cells were isotope transplanted into the breast, 4T1-luciferase breast cancer cells ($1\times10^5$) were injected into NOD-SCID mice as immunodeficient mice. From the time point when the tumor mass began to grow in the mammary gland No. 4 on 5 days after the injection, 175 nmol/kg of each of PBS, dKLA, MEL and MEL-dKLA was injected into each group once every 3 days. To measure the growth of the tumor, the size of the tumor was measured once every 3 days using a caliper device, and all tumor tissues were collected 4 weeks after the injection. On 4 weeks after the tumor transplantation, in order to identify metastasis of the tumor to the lymph nodes and lungs, D-luciferin as a substrate of luciferase enzyme was diluted to a concentration of 40 mg/ml and then, 100 μl thereof was administered to mice in an intraperitoneal administration mode. After reacting for about 15 minutes, luminescence was measured using NightOwl (Berthold Technologies) as an in vivo imaging device. Then, we analyzed the luminescence with pictures of mice to identify the level of metastasis to the whole body and lungs. The animal experiment was approved by the Animal Management Committee of Kyunghee University [KHUASP(SE)-18-133], and the animals were managed via autonomous feeding of water and food under a 12-hour light/dark cycle environment without pathogens.

Additionally, 4T1-luciferase breast cancer cells ($1\times10^5$) were injected into BALB/c mice through a tail vein in order to identify metastaticity of tumor cells. 3 days after the injection, 175 nmol/kg of each of PBS, dKLA, MEL and MEL-dKLA was injected into each group once every 3 days. 15 days after the cancer cell injection, D-luciferin as a substrate of luciferase enzyme was diluted to a concentration of 40 mg/ml, and then 100 μl thereof was administered to mice in an intraperitoneal administration mode, Then, reaction occurred for about 15 minutes. NightOwl (Berthold Technologies) was used in combination with photographs of mice to analyze the level of settlement and metastasis of cancer cells to the whole body and lungs.

As a result, as may be seen in FIGS. 10 to 11, it was identified that the breast cancer mass grew rapidly in the mammary gland in the PBS-treated group. In the group treated with MEL-dKLA, the growth of breast cancer cells was effectively reduced, while in the group treated with each of MEL and dKLA alone, the effect of reducing breast cancer growth did not occur significantly ((a), (b) and (c) of FIG. 10). It was identified based on the result of identifying metastasis to the lymph nodes of the armpit and to lungs that in the PBS-treated group, an area where metastasis occurred was large and the luminescence level at the metastasis site was very high. In the dKLA or MEL-treated group, there was no significant difference from the PBS-treated group in terms of the metastasis area, and the luminescence level exhibited a tendency to decrease but did not exhibit significance. It was identified that in the MEL-dKLA-treated group, substantially no metastasis was observed, and the metastasis area and the luminescence level were significantly reduced ((d) and (e) of FIG. 10).

Further, in the experiment to identify metastaticity of tumor cells, in the group treated with each of PBS and dKLA, the luminescence level of cancer cells was measured at a high level throughout the body. It was identified that in the MEL-treated group, metastasis was reduced compared to the PBS or dKLA-treated group. In the MEL-dKLA-treated group, the level of cancer cell luminescence in the lung was measured at a very low level. Throughout the whole body, the MEL-dKLA-treated group exhibited significantly lower metastaticity compared to the MEL-treated group (FIG. 11).

Thus, it was identified that MEL-dKLA significantly inhibited tumor growth and metastasis in breast cancer than the treatment with other peptides and the treatment with the anticancer drug alone did.

Example 5

Measurement of Expression Level of Tumor Metastasis Gene Due to Treatment With MEL-dKLA To measure the ability of MEL-dKLA to inhibit tumor metastasis, expression levels of CD44 known to interact with extracellular matrix ligand to promote metastasis and invasion and thus to be widely expressed in cancer, CCL22 known as M2-type macrophage marker, HIF-1α known as a marker of angiogenesis, metastasis and invasion, Ym1 as a marker of M2-type macrophage, and MMP-9 involved in the migration and settlement of tumor cells were measured via quantitative real-time PCR.

More specifically, RNA was extracted from lung tissue using an easy-BLUE RNA extraction kit (iNtRON Biotechnology, Korea). Then, cDNA was synthesized according to the manual for cyclescript reverse transcriptase (Bioneer, Korea). cDNA synthesis conditions were as follows: 15 seconds at 95, 10 seconds at 55, and 10 seconds at 72. Each reaction was conducted 3 times. Thereafter, CD44: forward, (SEQ ID NO: 4; 5'-TGGATCCGAATTAGC TGGA-3'); (SEQ ID NO: 5; reverse, 5'-GCTTTTTCTTCTGCCCACA-3'); CCL22: forward, (SEQ ID NO: 6; 5'-TCCCAGGG-GAAGGAATAAA-3'); reverse, (SEQ ID NO: 7; 5'-GGTTTGGATCAA GCCCTTT-3'); HIF-1α: forward, (SEQ ID NO: 8; 5'-TCCCTTTTTCAAGCAGCAG-3'); reverse, (SEQ ID NO: 9; 5'-TGCCTTGTATGGGAGCATT-3'); Ym-1: forward, (SEQ ID NO: 10; 5'-CAT-TCAGTCAGTTATCAGATTCC-3'); reverse, (SEQ ID NO: 11; 5'-AGTGAGTAGCAGCCTTGG-3'); MMP-9: forward, (SEQ ID NO: 12; 5'-TGAATCAGCTGGCTTTTGTG-3'); reverse, (SEQ ID NO: 13; 5'-GTGGATAGCTCG GTGGTGTT-3'); primer were used. Quantitative real-time PCR was performed using the SensiFAST SYBR no-Rox kit (Bioline, Korea).

As a result, as shown in FIG. 12, CD44 expression was significantly increased in the PBS-treated group compared to the WT-treated group. In the group treated with MEL-dKLA, the level of CD44 expression was significantly lower than that in the group treated with each of PBS, dKLA, and MEL alone ((a) of FIG. 12). The expression of CCL22 and HIF-1α increased in the PBS-treated group compared to the WT-treated group, and but significantly decreased in the MEL-dKLA-treated group. On the contrary, data of the group treated with each of dKLA and MEL was not significantly different from data of the PBS-treated group ((b) and (c) of FIG. 12). It was identified that in the dKLA-treated group, expression of Ym1 increased significantly compared to the PBS-treated group. Ym1 expression of the group treated with each of MEL and MEL-dKLA exhibited no significant difference from that of the PBS-treated group ((d) of FIG. 12). It was identified that the expression of MMP-9 was high in the PBS-treated group and the dKLA-treated group, and the expression of MMP-9 in the MEL-treated group was lower compared to that in the PBS-treated group. On the contrary, in the group treated with MEL-dKLA, the expression level of MMP-9 was found to be lower than that in the group treated with MEL ((e) of FIG. 12).

Thus, it was identified that MEL-dKLA has a markedly higher inhibitory effect on tumor metastasis factor expression than when each of MEL and dKLA was used alone.

Example 6

Analysis of MEL-dKLA Targeting CD206+ M2-Type Tumor-Associated Macrophage (TAM) Via Flow Cytometry In order to identify whether the MEL-dKLA peptide may be used as a peptide targeting M2-type tumor-associated macrophage (TAM) in vivo, tumor tissues were cultured, stained and analyzed individually to identify cell growth.

More specifically, the tumor cells were thinly crushed and separated from each other in DMEM to which DNaseI (1 U/mL) and collagenase D (1 mg/mL) were added. The tissue was gently agitated for 1 hour at 37° C., and separated using a 100-µM nylon mesh filter. Red blood cells were dissolved in Phrmlyse buffer (BE bioscience). Individual cells passed through a 40-µm nylon mesh filter and then were stained with following antibodies: CD4+ T cell (CD45+CD4+ CD8−), CD8+ T cell (CD45+CD4−CD8+), Foxp3+ regulatory T cell (CD4+CD25+Foxp3+), dendritic cell (CD45+ CD11b+CD11c+), and M1 (CD45+F4/80+CD86+) or M2 macrophage (CD45+F4/80+CD206+): anti-CD45-FITC, anti-CD4-phycoerythrin (PE), anti-CD8-allophycocyanin (APC), anti-CD4-FITC, anti-CD25-PE, anti-Foxp3-Alexa Fluor647, anti-CD11b-APC, anti-CD11c-APCcy7, anti-Grl-PEcy7, anti-CD86-PEcy7, and anti-CD206-APC antibodies. Annexin-V was previously treated to measure the cell percentage of macrophages.

As a result, as shown in FIG. 13, the F480+ CD86+ M1-type tumor-associated macrophage slightly increased in the MEL-administered group compared to the PBS and dKLA-administered groups. However, no significant difference between the F480+ CD86+ M1-type tumor-associated macrophage in the MEL-administered group and that in the dKLA-administered group could be identified. On the contrary, in the group administered with the MEL-dKLA, the F480+ CD86+ M1-type tumor-associated macrophage increased significantly compared to the MEL-administered group ((a) and (c) of FIG. 13). A proportion of M2-type tumor-associated F4/80+ CD206+ TAM in CD45+ leukocytes in each of the PBS and dKLA-administered groups was about 20%. In the MEL-administered group and the MEL-dKLA-administered group, the M2-type tumor-associated macrophage (TAM) cells decreased by half compared to the PBS-treated group. Thus, in the MEL-administered group and the MEL-dKLA-administered group, a proportion thereof was about 10% ((b) and (d) of FIG. 13). However, it was identified that the ratio of M1/M2 was significantly higher in the MEL-dKLA-administered group compared to that in the MEL-administered group. The M2-type tumor-associated macrophage (TAM) was significantly lowered in the MEL-administered group and MEL-dKLA-administered group compared to that in each of the PBS-administered group and the dKLA-administered group ((e) of FIG. 13). However, amounts of other leukocytes such as CD4 T cells, Foxp3+ Tregs, CD8 T cells and dendritic cells were not changed. Thus, each of MEL and MEL-dKLA may have no effect thereon ((f) and (i) of FIG. 13).

Further, in order to identify whether M2-type tumor-associated macrophage (TAM) cells were selectively killed in mice, M1-type tumor-associated macrophage (TAM) (F4/80 CD86+) and M2-type tumor-associated macrophage (TAM) (F4/80 CD206+) were stained with Annexin-V, respectively.

As a result, as shown in FIG. 14, an increase in Annexin-stained cells in CD86+ M1-type tumor-associated macrophage (TAM) was not observed in all groups, compared to the PBS-administered group as the control ((a) of FIG. 14). Further, reduction of the M2-type tumor-associated macrophage (TAM) occurred in each of the MEL and MEL-dKLA-administered groups. However, cell death of a significant amount of CD206+ M2-type tumor-associated macrophage (TAM) could only be identified in the MEL-dKLA administered group ((b) of FIG. 14). The apoptosis level caused by the administration of MEL-dKLA was significantly higher in M2-type tumor-associated macrophage (TAM) than in M1-type tumor-associated macrophage (TAM) ((c) of FIG. 14).

Thus, it was identified that MEL-dKLA selectively induced apoptosis of M2-type tumor-associated macrophage (TAM), and the ratio of M1/M2 was significantly increased compared to that when MEL was applied to the subject.

Example 8

Relationship Between CD206+ TAM Reduction in Tumor and Anti-Angiogenic Effect

CD31 (PECAM-1) is actively secreted from the vascular endothelium, and is well-known as a marker that may indicate angiogenesis. The angiogenesis in tumors is essential means to supply oxygen and nutrients to areas at a low oxygen level in the tumor and thus is closely related to cancer growth and metastasis. M2-type macrophages are major precursors of angiogenic factors, and contain cyclooxygenase-2, matrix metalloproteinase-9 and VEGF. The density of macrophage is related to angiogenesis. Therefore, immunostaining was performed and a confocal device was used to identify whether a decrease in the M2-type tumor-associated macrophage (TAM) in a tumor causes a decrease in angiogenesis.

More specifically, the tissue was dried with paraformaldehyde for 24 hours. Then, the tissue was cut into sections having 4 µm thickness using a rotary microtome, which in turn was restored via autoclaving under pressure for 1 minute with tri-sodium citrate buffer. The restored tissue sections were cultured together with anti-mouse serum endothelial cell adhesion material (PECAM; CD31) antibody (1:200; Santa Cruz Biotechnology, CA, USA) and anti-rabbit secondary antibody conjugated with Alexa-488 (1:500; Invitrogen) and were visualized by staining. After the staining, the sections were mounted on and analyzed using a laser scanning confocal microscope (Carl Zeiss). All images are taken using LSMS PASCAL, and fluorescence values were analyzed using ImageJ software.

As a result, as shown in FIG. 15, it was identified that a significant decrease in CD31+ endothelial cells occurred in both the MEL and MEL-dKLA treated groups ((a) and (b) of FIG. 15).

Thus, it was identified that the inhibition of angiogenesis was associated with the reduction of M2-type tumor-associated macrophage (TAM).

The concentration of TAM in the tumor stroma is closely related to tumor growth, metastasis, and angiogenesis. However, only the macrophage reduction method could not effectively solve the problems such as tumor growth and angiogenesis. The improved anticancer effect according to the present disclosure was thought to be related to the high ratio of M1/M2. MEL-dKLA according to the present disclosure selectively reduces M2-type tumor-associated macrophage (TAM) to effectively improve the ratio of M1/M2 and thus to induce death of mitochondria, such that tumor growth and angiogenesis were inhibited. Therefore, MEL-dKLA could be effectively used as a cancer treatment agent targeting the M2-type tumor-associated macrophage (TAM).

Based on the above descriptions, those skilled in the art to which the present disclosure belongs will understand that the present disclosure may be implemented in other specific forms without changing the technical idea or essential features. In this regard, the embodiments as described above are illustrative in all respects and should be understood as non-limiting. The scope of the present disclosure should be interpreted such that the scope of the present disclosure includes the meaning and scope of the claims to be described later, and all changes or modified forms derived from the equivalent concept rather than the details as description above.

---

The invention claimed is:

1. A melittin-anticancer drug conjugate in which melittin is conjugated with an anticancer drug, the anticancer drug being a pro-apoptotic peptide selected from the group consisting of KLA, alpha-defensin-1, BMAP-28, brevenin-2R, buforin IIb, cecropin A-magainin 2 (CA-MA-2), cecropin A, cecropin B, chrysophsin-1, D-K6L9, gomesin, lactoferricin B, LLL27, LTX-315, magainin 2, magainin II-bombesin conjugate (MG2B), pardaxin and combinations thereof.

2. A melittin-anticancer drug conjugate in which melittin is conjugated with an anticancer drug selected from the group consisting of entinostat, cladribine, pralatrexate, lorlatinib, maytansine DM1, maytansine DM3, maytansine DM4 and combinations thereof.

3. The melittin-anticancer drug conjugate of claim 1, wherein the conjugate targets an M2-type tumor-associated macrophage.

4. The melittin-anticancer drug conjugate of claim 1, wherein the conjugate has improved anticancer activity compared to the anticancer drug.

5. The melittin-anticancer drug conjugate of claim 1, wherein the melittin and the anticancer drug are conjugated to each other via a chemical linker, or the melittin and the anticancer drug are directly conjugated to each other.

6. The melittin-anticancer drug conjugate of claim 5, wherein the chemical linker binds to the melittin and the anticancer drug via an amine group, a carboxyl group or a sulfhydryl group on the melittin and the anticancer drug.

7. The melittin-anticancer drug conjugate of claim 5, wherein the chemical linker includes, at both ends thereof, a functional group selected from the group consisting of carbodiimide, N-hydroxysuccinimide ester (NHS ester), imidoester, pentafluropheny ester, hydroxymethyl phosphine, maleimide, haloacetyl, pyridyldisulfide, thiosulfonate, vinylsulfone, and combinations thereof.

8. The melittin-anticancer drug conjugate of claim 5, wherein the chemical linker is selected from the group consisting of EDC (1-ethyl-3-(3-dimethylaminopropyl)carbodiimide), DCC (N,N'-dicyclohexylcarbodiimide), SATA (succinimidyl acetylthioacetate), sulfo-SMCC (sulfosuccinimidyl-4-(NDmaleimidomethyl)cyclohexane-1-carboxylate), DMA (dimethyl adipimidate.2HCl), DMP (dimethylpimelimidate.2HCl), DMS (dimethyl Suberimidate.2HCl), DTBP (dimethyl 3,3'-dithiobispropionimidate.2HCl), sulfo-SIAB (sulfosuccinimidyl(4-iodoacetyl)aminobenzoate), SIAB (succinimidyl(4-iodoacetyl)aminobenzoate), SBAP (succinimidyl 3-(bromoacetamido)propionate), SIA (succinimidyl iodoacetate), SM(PEG)n (succinimidyl-([N-maleimidopropionamido]-#ethyleneglycol ester, wherein n=2, 4, 6, 8, 12 or 24), SMCC (succinimidyl-4-(N-Dmaleimidomethyl)cyclohexane-1-carboxylate), LCSMCC (succinimidyl 4-(N-maleimidomethyl)cyclohexane-1-carboxy-(6-amidocaproate)), sulfo-EMCS (N-εester), EMCS (N-εsulfo-GMBS(N-γester), GMBS (N-γ ester), sulfo-KMUS (N-κester), sulfo-MBS (m-maleimidobenzoyl-Nhydroxysulfosuccinimide ester), MBS (m-maleimidobenzoyl-N-hydroxysuccinimide ester), sulfo-SMPB (sulfosuccinimidyl 4-(p-maleimidophenyl)butyrate), SMPB (succinimidyl 4-(pmaleimidophenyl)butyrate), AMAS (N-α-maleimidoacet-oxysuccinimide ester), BMPS (N-β-maleimidopropyloxysuccinimide ester), SMPH (succinimidyl 6-[(β-maleimidopropionamido)hexanoate]), PEG12-SPDP (2-pyridyldithiol-tetraoxaoctatriacontane-N-hydroxysuccinimide), PEG4-SPDP, sulfo-LCSPDP (sulfosuccinimidyl 6-[3'-(2-pyridyldithio)propionamido]hexanoate), SPDP (succinimidyl 3-(2-pyridyldithio)propionate), LC-SPDP (succinimidyl 6-[3'-(2-pyridyldithio)propionamido]hexanoate), SMPT (4-succinimidyloxycarbonyl-alpha-methyl-alpha(2-pyridyldithio)toluene), DSS (disuccinimidyl suberate), BS (PEG)5 (bis(succinimidyl) penta (ethylene glycol)), BS(PEG)9 (bis(succinimidyl) nona (ethylene glycol)), BS3 (bis[sulfosuccinimidyl] suberate), BSOCOES (bis[2-(succinimidooxycarbonyloxy)ethyl] sulfone), PDPH (3-(2-pyridyldithio)propionyl hydrazide), DSG (disuccinimidyl glutarate), DSP (dithiobis[succinimidyl propionate]), BM(PEG)n (1,8-bismaleimido-ethyleneglycol, n=2 or 3), BMB (1,4-bismaleimidobutane), BMDB (1,4-bismaleimidyl-2,3-dihydroxybutane), BMH (bismaleimidohexane), BMOE (bismaleimidoethane), DTME (dithiobismaleimidoethane), TMEA (tris(2-maleimidoethyl)amine), DSS (disuccinimidyl suberate), DST (disuccinimidyl tartarate), DTSSP (3,3'-dithiobis[sulfosuccinimidylpropionate]), EGS (ethylene glycol bis [succinimidylsuccinate]), sulfo-EGS (ethylene glycol bis [sulfosuccinimidylsuccinate]), TSAT (tris-succinimidyl aminotriacetate), DFDNB (1,5-difluoro-2,4-dinitrobenzene), and combinations thereof.

9. A pharmaceutical composition for prevention or treatment of a tumor-associated macrophage-mediated disease, the composition comprising the conjugate of claim 1.

10. The pharmaceutical composition of claim 1, wherein the disease is selected from the group consisting of lung cancer, metastatic cancer, and breast cancer.

11. The pharmaceutical composition of claim 10, wherein the disease is Lewis lung cancer or inflammatory disease.

12. The pharmaceutical composition of claim 9, wherein the pharmaceutical composition is used for prevention or treatment of cancer growth and metastasis via removal of M2-type tumor-associated macrophage.

13. A method of preparing the melittin-anticancer drug conjugate of claim 1, the method comprising conjugating melittin and an anticancer drug to each other.

14. A method of preventing or treating a tumor-associated macrophage-mediated disease comprising
administering the melittin-anticancer drug conjugate of claim 1 to a subject in need thereof.

15. A method of preventing or treating a tumor-associated macrophage-mediated disease comprising administering the melittin-anticancer drug conjugate of claim 2 to a subject in need thereof.

16. The method of claim 14, wherein the anticancer drug is selected from the group consisting of doxorubicin, methotrexate, entinostat, cladribine, pralatrexate, lorlatinib, maytansine DM1, maytansine DM3, maytansine DM4 and combinations thereof.

17. The method of claim 14, wherein the tumor-associated macrophage-mediated disease is at least one selected from the group consisting of lung cancer, metastatic cancer, inflammatory disease, and breast cancer.

* * * * *